United States Patent [19]

Yoshida et al.

[11] Patent Number: 4,808,708
[45] Date of Patent: Feb. 28, 1989

[54] PHOSPHORSULFIDE DERIVATIVES OF DEOXYNUCLEOSIDES OR DEOXYNUCLEOTIDES AND THEIR USES

[75] Inventors: Tadao Yoshida; Kaoru Kimura, both of Nagoya, Japan

[73] Assignee: Toagosei Chemical Industry Co., Ltd., Tokyo, Japan

[21] Appl. No.: 925,890

[22] Filed: Oct. 30, 1986

[30] Foreign Application Priority Data

| Nov. 2, 1985 | [JP] | Japan | 60-245326 |
| Jul. 8, 1986 | [JP] | Japan | 61-158719 |
| Jul. 23, 1986 | [JP] | Japan | 61-171825 |
| Aug. 1, 1986 | [JP] | Japan | 61-180002 |

[51] Int. Cl.$^4$ .................................. C07H 17/00
[52] U.S. Cl. ........................... 536/27; 536/28; 536/29
[58] Field of Search ........................... 536/27, 28, 29

[56] References Cited

U.S. PATENT DOCUMENTS

| 3,804,826 | 4/1974 | Scheit et al. | 536/28 |
| 3,846,402 | 11/1974 | Eckstein et al. | 536/29 |
| 4,415,732 | 11/1983 | Caruthers | 536/27 |
| 4,521,509 | 6/1985 | Benkovic et al. | 435/6 |

OTHER PUBLICATIONS

Sekine et al., Tetrahedron, 41(22), pp. 5279–5288, 1985.
van Boekel et al., Chem. Lett., pp. 1725–1728, 1981.
Honeda et al., Tett. Lett., 22(22), pp. 2093–2096, 1981.
Mitsubishi, Chem. Abstr., 98:54407e, 54408f, p. 723, 1983.

Primary Examiner—Johnnie R. Brown
Assistant Examiner—L. Eric Crane
Attorney, Agent, or Firm—Cooper & Dunham

[57] ABSTRACT

Novel phosphorsulfide derivatives of deoxynucleosides or deoxynucleotides are provided, which have the general formula:

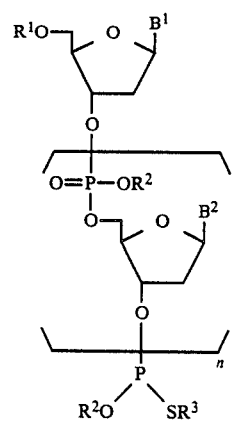

wherein $R^1$ is a hydroxy-protecting group; $R^2$ is a phosphate-protecting group; $R^3$ is an aryl group; $B_1$ and $B_2$ may be the same or different and each are a base residue which may have a protecting group; and n is zero or a positive integer, provided that if n is 2 or larger, the respective $R^2$ may be the same or different. They are prepared by reacting a deoxynucleoside or deoxynucleotide with a 1,2,4-triazolylphosphine compound and are useful as intermediates for the preparation of oligodeoxy-nucleotides.

13 Claims, 2 Drawing Sheets

PHOSPHORSULFIDE DERIVATIVES OF DEOXYNUCLEOSIDES OR DEOXYNUCLEOTIDES AND THEIR USES

FIELD OF THE INVENTION

This invention relates to novel phosphorsulfide derivatives of deoxynucleosides or deoxynucleotides and their uses, particularly for the preparation of oligodeoxynucleotides by the phosphite triester process so-called.

BACKGROUND OF THE INVENTION

For the purpose of preparing oligodeoxynucleotides, there have widely been used two processes, called phosphate triester process and phosphite triester process. In the phosphate triester process, a deoxynucleoside-3'-phosphate compound of general formula (A) shown below is usually used as an intermediate compound. The phosphite triester process, on the other hand, usually uses as an intermediate compound either a deoxynucleoside-3'-O-phosphorchloride compound of general formula (B) or a deoxynucleoside-3'-O-phosphoramidite compound of general formula (C) given below.

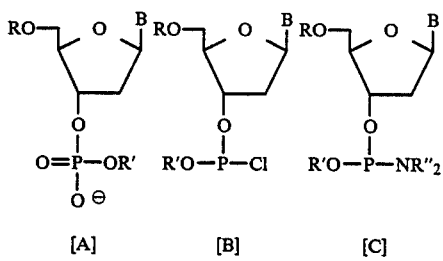

[A]  [B]  [C]

wherein R is a hydroxy-protecting group, R' is a phosphate- or phosphite-protecting group, R" is an alkyl group and B is a base residue which may have a protecting group. Details on the preparation and uses of compounds (A) are described in C. B. Reese, Tetrahedron, 34, 3143 (1978), those of compounds (B) are in R. L. Letsinger et al., J. Am. Chem. Soc., 97, 3278 (1975) and those of compounds (C) are in M. H. Caruthers et al., Tetrahedron Lett. 22, 1859 (1981), all the disclosures of which are incorporated by reference herein.

Main advantage of the phosphate triester process is in that compounds (A) are stable against oxygen and water with the ease in the preparation and handling thereof. This will be a primary reason why the said process has prevailingly been adopted for practical applications. However, the phosphate triester process has such inconvenience that the condensation reaction of a compound (A) with a 5'-O-deoxynucleoside or a 5'-O-deoxynucleotide, so-called internucleotide-forming reaction, is not so fast as desired, requiring a relatively long time to obtain oligomers intended.

On the other hand, the phosphite triester process wherein compounds (B) or (C) are used has an advantage that both compounds (B) and (C) exhibit high reactivities on the alcoholic hydroxyl group of 5'-O-deoxynucleosides or 5'-O-deoxynucleotides, thus can bring a rapid internucleotide-forming reaction to afford desired oligodeoxynucleotide product with much less reaction time than that required in the phosphate triester process. In particular, the phosphite triester process is effectively applicable to solid phase processes for the preparation of oligodeoxynucleotides. However, compounds (B) and (C), particularly compounds (B), have such drawbacks that their preparation and handling are not simple or easy, that they are unstable to oxygen and water, so that care must be taken to avoid their decomposition during storage and use, and the like. In fact, it is known that compounds (B) are generally so unstable as to be difficult to isolate them from the reaction system in their preparation and that compounds (C) are also unstable to such extent that their P-N bond is readily severed even in the presence of a weak acid.

In the light of the level of the prior art as explained above, we have investigated on the preparation of oligodeoxynucleotides with the main intention of looking for useful intermediate compounds therefor in the sense that they can easily be prepared, are stable under storage and convertible readily and rapidly to desired oligodeoxynucleotides and have now synthesized, for the first time, phosphorsulfide derivatives of deoxynucleosides and of deoxynucleotides of the structure hereinafter specified which are advantageously adaptable for the purpose as intended above.

SUMMARY OF THE INVENTION

Accordingly, a primary object of this invention is to provide novel phosphorsulfide derivatives of deoxynucleosides or deoxynucleotides which are useful as intermediates for the preparation of oligodeoxynucleotides.

Another object of this invention is to provide a process for the preparation of oligodeoxynucleotides starting from the novel phosphorsulfide derivatives.

These and other objects of this invention will become clear from the descriptions hereinafter given.

According to the first aspect of this invention, therefore, there is provided a phosphorsulfide derivative of a deoxynucleoside or deoxynucleotide of general formula (I)

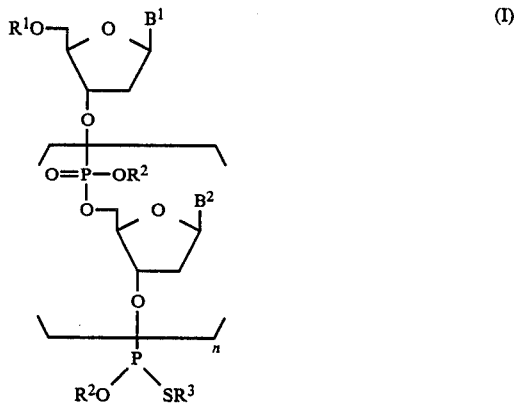

wherein $R^1$ is a hydroxy-protecting group; $R^2$ is a phosphate-protecting group; $R^3$ is an aryl group; $B_1$ and $B_2$ may be the same or different and each are a base residue which may have a protecting group; and n is zero or a positive integer, provided that if n is 2 or larger, the respective $B_2$ may be the same or different.

The most typical compounds of general formula (I) according to this invention include those of two types having general formulae (IA) and (IB), respectively.

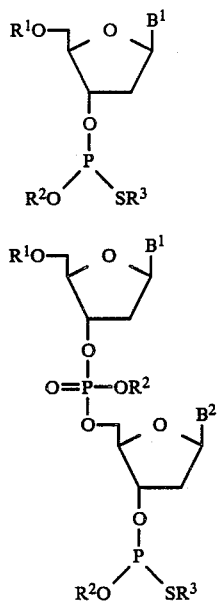

wherein $R^1$, $R^2$, $R^3$, $B^1$ and $B^2$ have the meanings as defined above. Clearly, compounds of general formula (IA) are deoxynucleoside-3'-O-phosphorsulfides which correspond to compounds of general formula (I) where n=0 and compounds of general formula (IB) are dideoxynucleotide-3'-O-phosphorsulfides which correspond to compounds of general formula (I) where n=1.

DETAILED DESCRIPTION OF THE INVENTION

The following detailed descriptions given by way of illustration of this invention will rely mainly on those compounds of general formulae (IA) and (IB), but it should be understood that higher oligomeric compounds of general formula (I) where n=2 or larger integers can also be provided and used in the same manners as those given in respect of the compounds of general formula (I) where n=0 or 1, i.e. of general formulae (IA) and (IB).

As hydroxy-protecting group $R^1$ in general formula (I), there may be used, fundamentally, any of those known to be useful for protecting hydroxyl groups. Typically, there may be used those known to be useful for said purpose in the preparation of oligonucleotides, for example a triarylmethyl group such as triphenylmethyl, 4-methoxytriphenylmethyl, 4,4'-dimethoxytriphenylmethyl, etc.; pixyl (i.e. 9-phenylxanthen-9-yl) group; an alkoxycarbonyl group; an aryloxycarbonyl group; an arylthio-alkyloxycarbonyl group; and a trialkylsilyl group such as t-butyldimethylsilyl. The choice of a particular group from among those exemplified above as the hydroxy-protecting group $R^1$ for a particular compound of general formula (I) is not critical, but a triarylmethyl group is a preferred one as $R^1$ for the reason that it can be easily introduced into, and easily removed from, a deoxynucleoside or deoxynucleotide moiety and that some 5'-O-triarylmethyl-N-protected deoxynucleosides are commercially available.

As phosphate-protecting group $R^2$ in general formula (I), there may be used, fundamentally, any of those known to be useful for protecting a phosphate moiety. Typically, there may be used those known to be useful for said purpose in the preparation of oligonucleotides, for example a lower alkyl containing up to 5 carbon atoms, allyl, an arylsulfonylalkyl, an aryl, a haloaryl group, etc. The choice of a particular group from among those exemplified above as phosphate-protecting group $R^2$ for a particular compound of general formula (I) is not critical, but methyl, allyl, β-cyanoethyl and 2-chlorophenyl groups are most preferably selected as they have been studied widely and confirmed to be useful as phosphate-protecting group for the preparation of oligonucleotides.

Substituent $R^3$ in compounds of general formula (I) may be any aryl group, for example phenyl, 2-methylphenyl, 4-methylphenyl, 2,4-dimethylphenyl, 2,6-dimethylphenyl, 2,4,6-trimethylphenyl, 2-chlorophenyl, 4-chlorophenyl, 3,4-dichlorophenyl, α-naphthyl, etc. The specific nature of substituent $R^3$, an aryl group, to be chosen for a particular compound of general formula (I) depends upon the nature of phosphate-protecting group $R^2$ in said particular compound, but in general substituent $R^3$ is preferably selected from o-substituted aryl groups such as 2-methylphenyl, 2,6-dimethylphenyl, 2-chlorophenyl, etc. in view of ease in preparation and of high stability of the compounds of general formula (I) having such substituent $R^3$.

Exemplary base residues $B^1$ and $B^2$ in general formula (I) may include the thymine residue of formula (II) which may be protected on the 3-position, cytosine residues of formula (III) which may be protected on the 4-amino-substituent, adenine residues of formula (IV) which may be protected on the 6-amino-substituent and guanine residues of general formula (V) which may be protected on the 1-amido, 2-amino and 6-keto groups.

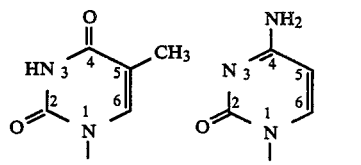

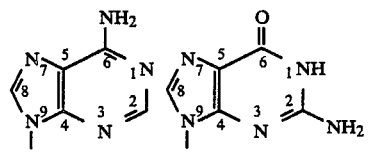

The nature of the protecting groups usable on the base residues of $B_1$ and $B_2$ is not limited, but it is preferred in general to use such groups as have been proposed as appropriate for the preparation of oligonucelotides, typically triarylmethyl, trialkylsilylalkyl, arythioalkyl, phthaloyl, aryloxycarbonyl, alkoxycarbonyl, dialkylcarbamoyl, diarylcarbamoyl, arylcarbonyl, alkylcarbonyl and 1,2-dialkylcarbonyloxyethylene groups. The choice of a particular protecting group for each of the base residues of formulae (II)-(V) above is within the level of the prior art as reported in many publications refer, for example, to Tsujiaki Hata et al., J. Soc. Org. Syn. Chem., Japan, 42, 429 (1984).

Typical, non-limited examples of the compounds of general formula (I) where n=0, corresponding to general formula (IA) are given below:

5'-O-dimethoxytritylthymidine-3'-O-(2-chloro-
  phenyloxy-2-methylphenylthio)phosphine;
5'-O-dimethoxytritylthymidine-3'-O-(methoxy-2-
  methylphenylthio)phosphine;
5'-O-dimethoxytritylthymidine-3'-O-(2-chloro-
  phenyloxy-2,6-dimethylphenylthio)phosphine;
5'-O-dimethoxytrityl-N$^4$-benzoyl-2'-deoxycytidine-3'-
  O-(2-chlorophenyloxy-2-methylphenylthio)phos-
  phine;
5'-O-dimethoxytrityl-N$^6$-phthaloyl-2'-deoxyadenosine-
  3'-O-(2-chlorophenyloxy-2-methylphenylthio)phos-
  phine;
5'-O-methoxytrityl-O$^6$-diphenylcarbamoyl-N$^2$-propio-
  nyl-2'-deoxyguanosine-3'-O-(2-chlorophenyloxy-2-
  methylphenylthio)phosphine;
5'-O-dimethoxytritylthymidine-3'-O-(allyloxy-2-
  methylphenylthio)phosphine; and
5'-O-dimethoxytritylthymidine-3'-O-(2-cyanoethyloxy-
  2-methylphenylthio)phosphine.

Typical, non-limited examples of the compounds of general formula (I) where n=1, corresponding to general formula (IB) are given below:

P-2-chlorophenyl-5'-O-dimethoxytritylthymidyl-3'-O-
  [(2-chlorophenyloxy-2-methylphenylthio)phos-
  phino]-(3'→5')thymidine;
P-2-chlorophenyl-5'-O-dimethoxytrityl-N$^4$-benzoyl-2-
  deoxycytidyl-3'-O-[(2-chlorophenyloxy-2-methyl-
  phenylthio)phosphino]-(3'→5')thymidine;
P-2-chlorophenyl-5'-O-dimethoxytrityl-N$^6$-benzoyl-2'-
  deoxyadenyl-3'-O-[(2-chlorophenyloxy-2-methyl-
  phenylthio)phosphino]-(3'→5')thymidine; and
P-2-chlorophenyl-5'-O-methoxytrityl-N$^2$-i-butyryl-2'-
  deoxyguanosinyl-3'-O-[(2-chlorophenyloxy-2-
  methylphenylthio)phosphino]-(3'→5')thymidine.

According to this invention, the phosphorsulfide derivatives of deoxynucleosides or deoxynucleotides of general formula (I) may be prepared in high yield by reacting a deoxynucleoside or deoxynucleotide of general formula (VI):

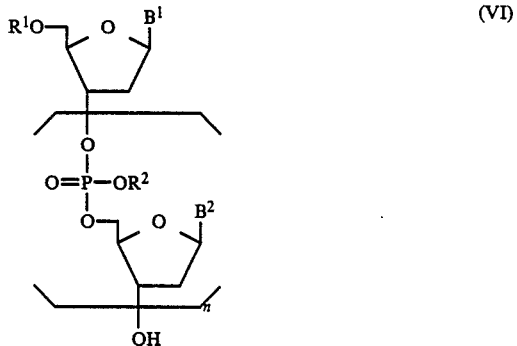

(VI)

wherein R$^1$, R$^2$, B$^1$, B$^2$ and n have the meanings as defined above with a 1,2,4-triazolylphosphine compound of general formula (VII):

(VII)

wherein R$^2$ and R$^3$ have the meanings as defined above. This reaction may be represented by the following equation:

(VI)   (VII)   →

(I)

Reaction (1) may preferably be carried out in an organic solvent. Typically, such organic solvent may be chloroform, methylene chloride, 1,2-dichloroethane, benzene, tetrahydrofuran, p-dioxane, etc. The solvent may preferably be dehydrated with a suitable drying agent and then purified by, for example, distillation prior to its use. The molar ratio of compound (VI) to compound (VII) to be used in said reaction (1) may usually be in the range of 1:1–1:10, but is preferably in the range of 1:1–1:2 to maximize the economic efficiency of the overall process. In practical operations, it is desirable, to slowly add a solution of compound (VII) dissolved in an organic solvent selected from the list supra to a solution or suspension of compound (VI) in the same organic solvent. The reaction may preferably be conducted at a temperature in the range of 0° C.–35° C. The reaction time required may depend upon various factors including the molar ratio of compounds (VI) and (VII) and the nature each of protecting groups R$^1$ and R$^2$, substituent R$^3$ and base residues B$^1$ and B$^2$ and may generally be in the range of 10 minutes to 2 hours. The completion of the reaction should preferably be confirmed by, for example, thin-layer chromatography (TLC), $^1$HNMR spectrometry, etc.

The compounds of general formula (I) thus prepared, that is deoxynucleosido- or deoxynucleotido-phosphorsulfides, may be used as such without isolation from the resulting reaction mixture, namely in situ in the solution resulting from the reaction between compounds (VI) and (VII) according to reaction (1) above for a subsequent reaction. But usually said compounds are used after having been isolated from the reaction mixture by, for example, the following method. Thus, the reaction solution, having confirmed the completion of the desired reaction, may be washed with a saturated aqueous sodium chloride solution and the like and the organic layer may be dried over anhydrous magnesium sulfate and the like and then subjected to distillation in vacuo to remove a substantial amount of the organic solvent used. The concentrated solution containing compound (I) may then be added dropwise to n-pentane or n-hexane to precipitate compound (I) in the form of fine powder which may then be separated by filtration and dried in vacuo. Alternatively, the concentrated solution of compound (I) above may be subjected to silica gel-column chromatography using chloroform, methylene chloride or ethyl acetate as eluent and the eluate containing compound (I) may be concentrated in vacuo to dryness thereby permitting isolation of compound (I) in the form of a foamed solid.

Compounds of general formula (I) of this invention are stable under storage for a relatively long period of time. For example, 5'-O-dimethoxytritylthymidine-3'-(2-chlorophenyloxy-2-methylphenylthio)phosphine and P-2-chlorophenyl-5'-O-dimethoxytritylthymidyl-3'-O-[(2-chlorophenyloxy-2-methylphenylthio)phosphino]-(3'→5')thymidine can be stored for 5 months at −20° C. without any sign of decomposition or other change.

Deoxynucleosides of general formula (VI) where n=0 to be used as starting compound for reaction (1) above for the preparation of compounds of general formula (I) according to this invention may be prepared by known processes (refer, for example, to Tsujiaki Hata et al., J. Soc. Org. Syn. Chem., Japan, 42, 429 (1984) and literature cited therein) or are commercially available. It is advisable that these compounds are dried as completely as possible by any suitable means before use.

Similarly, deoxynucleotides of general formula (VI) where n is a positive integer, typically 1, represented by general formula (VI') shown below, to be used as starting compound for reaction (1) above for the preparation of compounds of general formula (I) according to this invention may be prepared by known processes, for example those based on reaction (2) and reaction (3) given below which are described by P. Cashion et al., Tetrahedron Lett., 1976, 3769 and M. S. Poonian et al., J. Org. Chem., 49, 4905 (1984), respectively, for example,

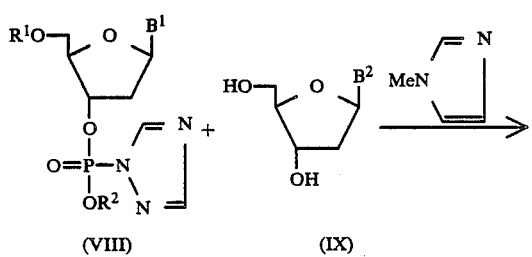

(VIII)   (IX)

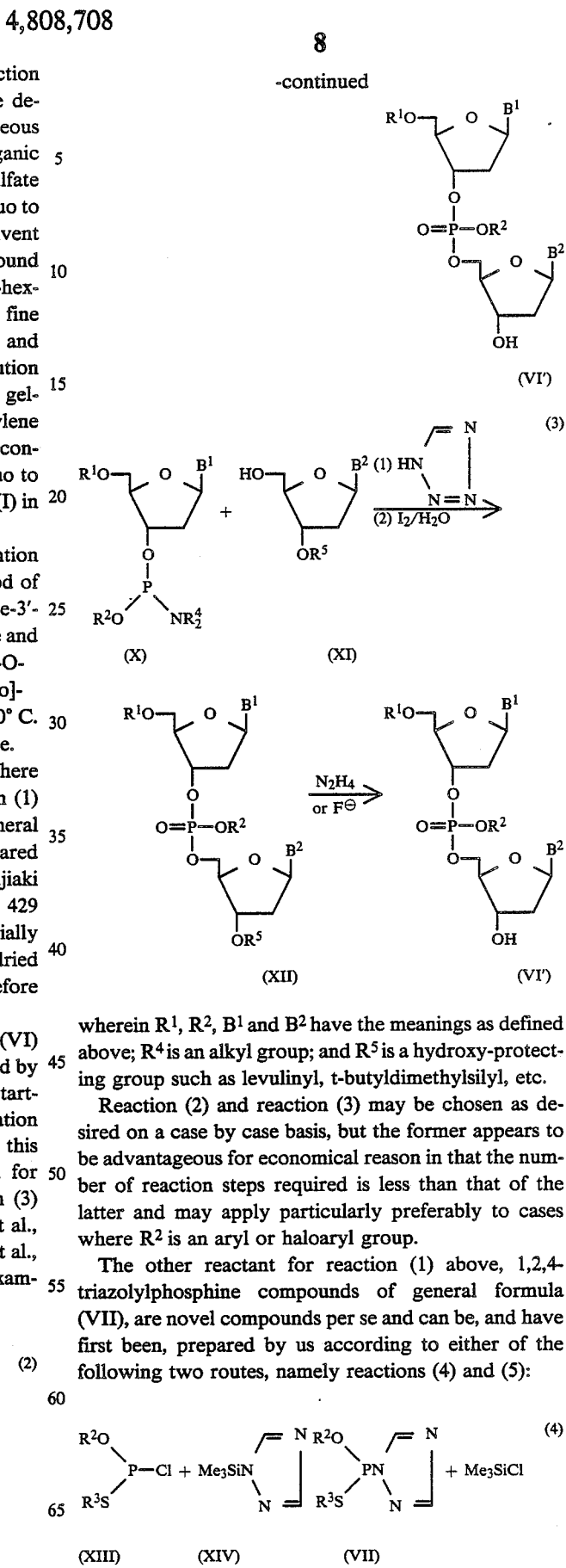

wherein $R^1$, $R^2$, $B^1$ and $B^2$ have the meanings as defined above; $R^4$ is an alkyl group; and $R^5$ is a hydroxy-protecting group such as levulinyl, t-butyldimethylsilyl, etc.

Reaction (2) and reaction (3) may be chosen as desired on a case by case basis, but the former appears to be advantageous for economical reason in that the number of reaction steps required is less than that of the latter and may apply particularly preferably to cases where $R^2$ is an aryl or haloaryl group.

The other reactant for reaction (1) above, 1,2,4-triazolylphosphine compounds of general formula (VII), are novel compounds per se and can be, and have first been, prepared by us according to either of the following two routes, namely reactions (4) and (5):

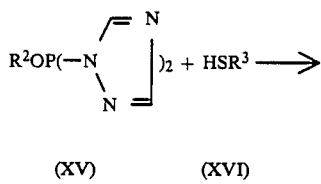

(XV)     (XVI)

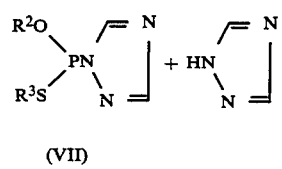

(VII)

wherein $R^2$ and $R^3$ have the meanings as defined above and Me is methyl group, details of which are given in Japanese patent application No. 165546/86 filed on July 16, 1986 and are incorporated herein by reference.

The choice of either of reactions (4) and (5) in each particular case may depend, at least partly, on the availability of starting compounds (XIII) and (XV).

Reaction (4) can rapidly proceed in an organic solvent such as chloroform, methylene chloride, benzene, toluene, etc. In view of the fact that compounds (VII) are not very stable in water, the organic solvent should preferably be dried by a suitable drying agent and then purified by distillation before use. The mole ratio of compound (XIII) to compound (XIV) may be in the range of 1:1–1:5, but preferably in the range of 1:1–1:1.5 with a view to maximizing the economy of the overall process. The reaction temperature may usually be in the range of 0° C.–35° C. The reaction time required may depend upon various factors including the mole ratio of compounds (XIII) and (XIV) and the nature of organic groups $R^2$ and $R^3$ and may generally be in the range of 5–30 minutes. Preferably, the completion of reaction should be confirmed by the usual means such as $^1$HNMR spectrometry.

Compounds (XIII) to be used as starting compounds for reaction (4) may be prepared by a known method as, for example, described in the literature (e.g. G. M. Kosolapoff et al., "Organic Phosphorus Compounds", Vol. 5, published by John Wiley & Sons (New York) in 1973 and references cited therein) according to reaction (6):

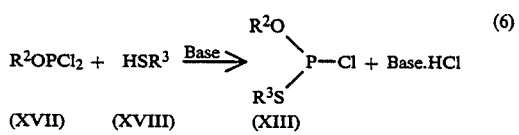

wherein $R^2$ and $R^3$ have the meanings as defined above and Base is an organic base such as triethylamine and pyridine.

Compounds (XIV) to be used as the other starting compound for reaction (4) may be prepared by a known method as, for example, described in the literature (e.g. L. Birkofer et al., Chem. Ber., 93, 2804 (1960) and references cited therein) according to reaction (7):

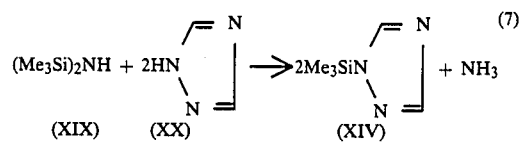

Usually, compounds (XIV) are commercially available.

Reaction (5) can proceed smoothly in an organic solvent such as chloroform, methylene chloride, benzene, toluene, etc., which has preferably been dried and purified before use as explained above. The molar ratio of compounds (XV) to (XVI) may desirably be in the range of 1:1–1:1.1. The reaction temperature may preferably be in the range of 0° C.–35° C. The reaction time required may depend upon various factors including the nature of organic groups $R^2$ and $R^3$ and may generally be in the range of 30 minutes–3 hours. Preferably, the completion of the reaction should be confirmed by the usual means such as $^1$HNMR spectrometry.

Compounds (XV) to be used as starting compounds for reaction (5) may be prepared by a known method as, for example, described in the literature (e.g. J. Fourrey et al., Tetrahydron Lett., 25, 4511 (1984) and references cited therein) according to reaction (8)

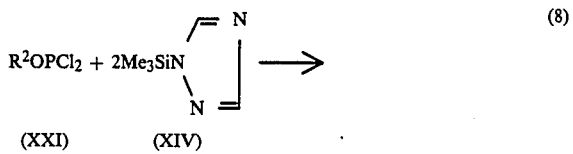

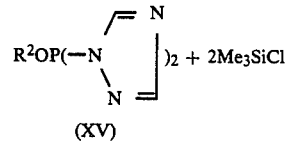

1,2,4-Triazolylphosphine compounds of general formula (VII) prepared according to either of reactions (4) and (5) above are not so stable to heat and water as to be purifyable and isolatable by chromatography or distillation, but the actual formation of compounds (VII) in substantially pure form and in substantially quantitative yield through reaction (4) or (5) has been confirmed as shown by points (a) and (b):

(a) After the completion of the intended reaction, the organic solvent used and the by-products were distilled off under reduced pressure and the $^1$HNMR of the residue showed signals due to the corresponding $R^2$ and $R^3$ groups and triazolyl group of compound (VII).

(b) The residue obtained as in (a) above was dissolved in an organic solvent, typically chloroform, and an alcohol, typically methanol, was added to the resulting solution in an equimolar proportion whereby an alcoholysis reaction occurred, which afforded a diorganoxy-organothiophosphine and 1,2,4-triazole in high yield according to reaction (9):

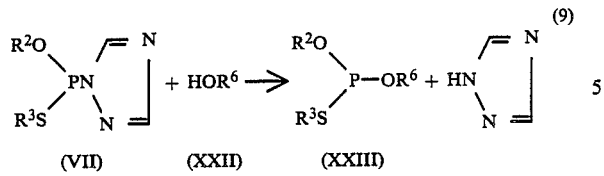

(VII)  (XXII)  (XXIII)

wherein $R^2$ and $R^3$ have the meanings as defined above and $R^6$ is an alkyl group.

The phosphorsulfide derivatives of deoxynucleosides or deoxynucleotides of general formula (I) according to this invention have been found to be advantageously applicable as an intermediate to the preparation of oligodeoxynucleotides, because of their ease in storage and handling, their high stability, as well as their high reactivity in the preparation disclosed.

According to a further aspect of this invention, therefore, there is provided an application of the compounds of general formula (I) of this invention as intermediates for the preparation of oligodeoxynucleotides, that is there is provided a process for the preparation of an oligodeoxynucleotides of general formula (XXIV):

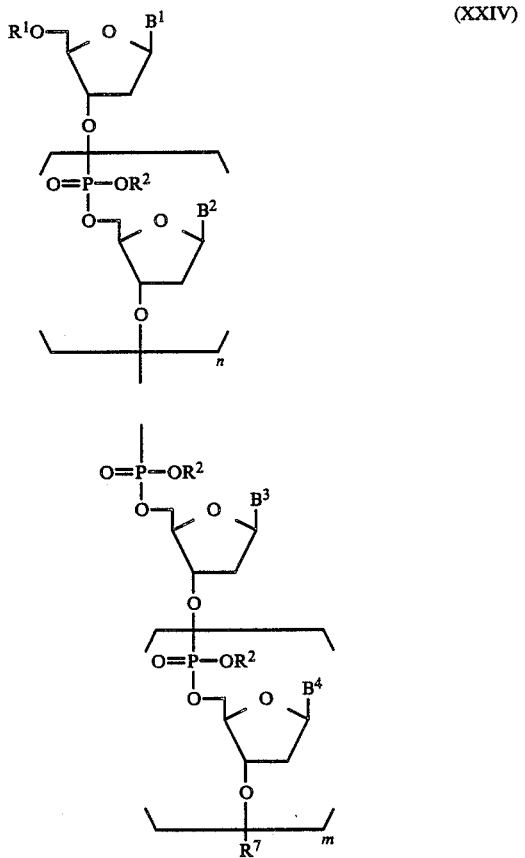

wherein $R^1$ is a hydroxy-protecting group; $R^2$ is a phosphate protecting group; $R^7$ is a hydroxy-protecting group which may contain a polymer-support; $B^1$, $B^2$, $B^3$ and $B^4$ may be the same or different and each is a base residue which may have a protecting group; n is zero or a positive integer; and m is zero or a positive integer, provided that if n and/or m is 2 or larger, respective $B^2$ and/or $B^4$ may be the same or different, which comprises reacting a phosphorsulfide derivative of a deoxynucleoside or deoxynucleotide of general formula (I):

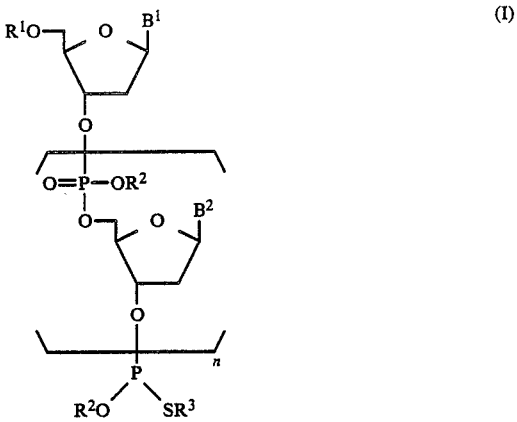

wherein $R^1$, $R^2$, $B^1$, $B^2$ and n have the meanings as defined above and $R^3$ is an aryl group with a deoxynucleoside or deoxynucleotide compound of general formula (XXV):

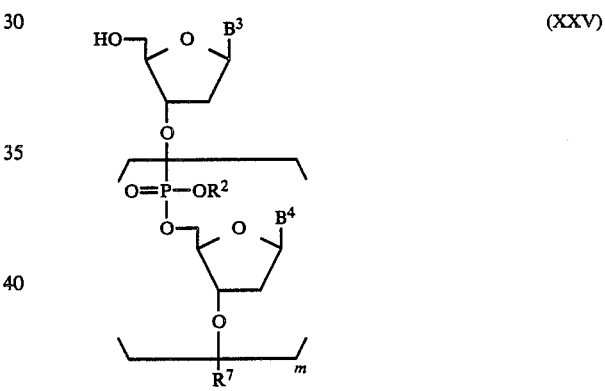

wherein $R^2$, $R^7$, $B^3$, $B^4$ and m have the meanings as defined above in the presence of a trialkylstannyl azole compound of general formula (XXVI) and a base of general formula (XXVII):

wherein $R^8$ is an alkyl group; $R^9$ is hydrogen atom or an alkyl or aryl group; $R^{10}$ is an alkyl group or both $R^{10}$'s together with the adjacent nitrogen atom represent a heterocyclic group which may contain one or two additional heteroatoms selected from nitrogen, oxygen and sulfur atoms; and X is an azolyl group: followed by oxidizing the resulting reaction product.

Thus, the reaction involved in the above preparation may be represented by reaction (10):

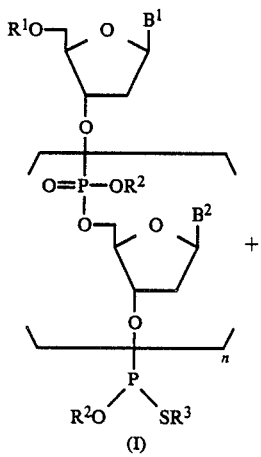

(I)

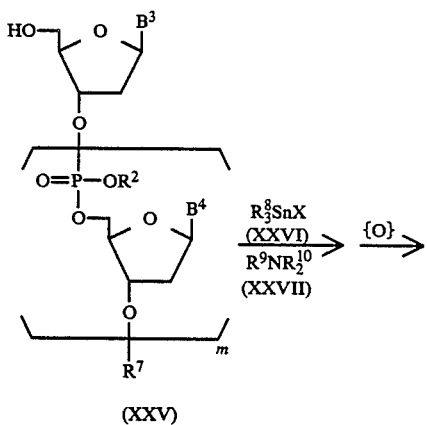

(XXV)

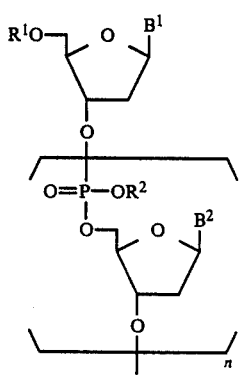

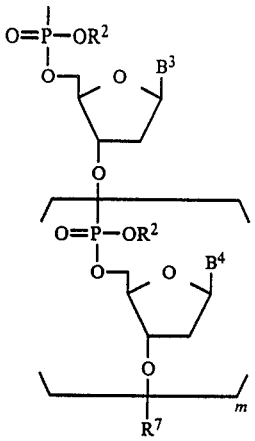

(XXIV)

Reaction (10) according to this invention generally comprises a coupling reaction between compound (I) and compound (XXV) in the presence of compound (XXVI) and compound (XXVII), and a subsequent oxidation of the phosphorus (III) atom of the resulting product. The coupling reaction between compounds (I) and (XXV) may smoothly proceed in an organic solvent such as for example methylene chloride, chloroform, 1,1-dichloroethane, 1,2-dichloroethane, tetrahydrofuran, p-dioxane, benzene and toluene. The solvent may preferably be dried by a suitable drying agent and then purified by, for example, distillation, before use. The reaction may be carried out at a temperature of 0° C.–35° C. and usually at room temperature. The molar proportions of compounds (I), (XXV), (XXVI) and (XXVII) may generally be 1–40 equivalents of compound (I), 1–100 equivalents of compound (XXVI) and 1–200 equivalents of compound (XXVII) all with respect to 1 equivalent of compound (XXV). This reaction may generally be completed within one hour, but it is preferable to confirm the completion of the reaction by usual means such as TLC and $^1$HNMR, particularly when the reaction is conducted in the liquid phase, that is when the hydroxy-protecting group $R^7$ of compound (XXV) is acetyl, benzoyl, levulinyl or t-butyldimethylsilyl group as hereinafter shown, and before the start of the subsequent oxidation reaction. On the other hand, when the reaction is effected in the solid phase, that is when group $R^7$ is an organic group of general formula (XXVIII) which contains a polymer-support as hereinafter shown, the completion of the reaction cannot be confirmed by TLC, $^1$HNMR, etc. In such cases, the time required for the completion of reaction may usually be determined by a method comprising conducting the coupling reaction for a certain predetermined period of time, then carrying out the oxidation reaction, removing hydroxy-protecting group $R^1$ from the resulting product of general formula (XXIV) and analyzing the amount of such deprotected $R^1$. In this case, if group $R^1$ is a triarylmethyl derivative such as dimethoxytrityl or monomethoxytrityl, the determination of the time required for the completion of reaction may easily be made by measuring the absorbance of trityl cation resulting from the removal of the protecting group $R^1$ by the action of an acid (so-called trityl cation test, where dimethoxytrityl cation is tested at 498 nm and monomethoxytrityl cation is tested at 475 nm).

The subsequent oxidation reaction may be effected by using an iodine-water system, m-chloroperbenzoic acid, iodobenzene diacetate, nitrogen oxide, etc. The choice of a particular oxidizing reagent for each particular case is not limited, but the use of iodine-water system is most preferable because of ease in availability and low cost. When the iodine-water system is used, the oxidation reaction may be conducted with 1-200-fold of the oxidizing reagent stoichiometrically required for the reaction intended, wherein the reaction may take only 1-5 minutes at a temperature of $-78°$ C.-$35°$ C.

When the trialkylstannyl azole compounds of formula (XXVI) are used for reaction (10), $R^8$ may be any of alkyl groups including primary, secondary and tertiary one such as methyl, ethyl, n-propyl, n-butyl, i-propyl, sec-butyl, tert-butyl, etc. The choice of a particular alkyl group from among those of various types for each particular case is not limited or critical, but may depend upon the ease in the preparation of compounds (XXVI) and their stability and other properties. Preferred alkyl groups as $R^8$ may include ethyl, n-propyl and n-butyl. Azolyl group X may be exemplified as imidazolyl, 3-nitroimidazolyl, benzimidazolyl, 1,2,3-triazolyl, 1,2,4-triazolyl, 3-nitro-1,2,4-triazolyl, benzotriazolyl, 5-chlorobenzotriazolyl, 5-nitrobenzotriazolyl, tetrazolyl, etc. The choice of a particular azolyl group from among those listed above for each particular case is also not limited, but may depend upon the case in the preparation of compounds (XXVI) and their effectiveness in the running of the reaction intended. Preferred azolyl groups as X may include imidazolyl, 1,2,3-triazolyl, 1,2,4-triazolyl, benzotriazolyl and tetrazolyl.

The trialkylstannyl azole compounds of general formula (XXVI) may be prepared advantageously by a process proposed by us in Japanese patent application No. 165,858/85 filed on Aug. 1, 1985 which involves reaction (11):

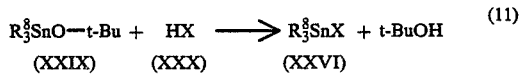  (11)

where $R^8$ and X have the meanings as defined above and t-Bu is tert-butyl group. According to this method, the desired compound (XXVI) can be obtained in quantitative yield simply by mixing compound (XXIX) with compound (XXX), preferably in an organic solvent such as methylene chloride and chloroform, usually at room temperature, though the range of $0°$ C.-$35°$ C. may be used. The mole ratio of compounds (XXIX) to (XXX) may generally be 1:1-2:1. The reaction (11) may proceed very rapidly and may usually take only 5-10 minutes.

Compounds of general formula (XXIV) to be used for reaction (11) may easily be prepared by a known method as, for example, described in U.S. Pat. No. 2,745,820 to G. P. Mack which involves the reaction (12) between a trialkyltin chloride (XXXI) and an alkali metal t-butoxide (XXXII).

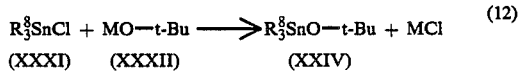  (12)

where $R^8$ and t-Bu have the meanings as defined above and M is an alkali metal.

Azoles of general formula (XXX) to be used for reaction (11) may of course be selected depending upon the nature of compound (XXVI) intended. They may be readily prepared by any known method or are commercially available and preferably dried as complete as possible before use.

Compound of general formula (XXVI) thus prepared according to reaction (11) may be used for a subsequent reactio without isolation from the reaction solution, but may usually be isolated, for example, by adding either or acetone to the resulting reaction solution to precipitate it as crystals or by distilling off the organic solvent used and t-butanol under a reduced pressure.

Compounds of general formula (XXVI) may also be prepared by known processes such as those described in Luijten et al., Rec. Trav. Chim., 82, 1181 (1963) and Dou Henri et al., Fr. Demande 2,342,728, the disclosure of which are incorporated herein by reference.

Base compounds of general formula (XXVII) to be used for reaction (10) according to this invention may include those wherein $R^9$ is hydrogen atom, an alkyl (e.g. methyl, ethyl, n-propyl, i-propyl, n-butyl, etc.) or an aryl (e.g. phenyl, 4-methylphenyl, etc.) and each $R^{10}$ is an alkyl (e.g. methyl, ethyl, n-propyl, i-propyl, n-butyl, etc.) or two $R^{10}$'s together with the adjacent nitrogen atom form a heterocyclic group which may contain one or two further hetero atoms selected from nitrogen, oxygen and sulfur atoms (e.g. piperidino, 2,6-dimethylpiperidino, pyrrolyl, morpholino, thiomorpholino, imidazolyl, 2-methylimidazolyl, benzimidazolyl, 1,2,4-triazolyl, 3-methyl-1,2,4-triazolyl, etc.) and those wherein $R^9$ and two $R^{10}$s together form with the adjacent nitrogen atom a heterocyclic group which may contain one or two further hetero atoms selected from nitrogen, oxygen and sulfur atoms such as pyridine, 2,6-dimethylpyridine, 4-dimethylaminopyridine, oxazole, thiazole, pyrimidine, pyrazine, quinoline, s-triazine, etc. The choice of a particular compound of general formula (XXVII) for each particular case is not limited, but those have a pKa value of 5-12 are preferable.

In the deoxynucleoside or deoxynucleotide compounds of general formula (XXV) to be used for reaction (10) according to this invention, $R^2$ is as defined and exemplified hereinbefore for general formula (I) and $B^3$ and $B^4$ are as defined for general formula (XXIV) and are the same as exemplified for $B^1$ and $B^2$ hereinbefore in respect of general formula (I).

Hydroxy-protecting group $R^7$ may fundamentally be any of 3'-hydroxy-protecting groups known to be suitable for the preparation of oligodeoxynucleotides, typically acetyl, benzoyl, levulinyl, t-butyldimethylsilyl or an organo-group having a polymer-support, as shown by general formula (XXXIII):

  (XXXIII)

wherein Ⓟ is a polymer-support and $Y_1$ and $Y_2$ may be the same or different and each are an organo-group capable of bonding to the adjacent polymer-support amide groups and carbonyl groups by covalent bonds. Typical examples of polymer-supports include silica gel and polystyrene. $Y_1$ and $Y_2$ may often be an alkylene group containing 1-10 carbon atoms though they are not so limited. The choice of protecting group $R^7$ may depend upon the form of reaction (10). Thus, if a liquid phase homogeneous reaction is applied, the use of acetyl, benzoyl, t-butyldimethylsilyl, etc. is preferred, whereas the use of organo-group of general formula (XXXIII) is suitable in a solid phase heterogeneous reaction.

In the compounds (XXV), m may be dependent upon the chain length of the object products of general formula (XXIV). Generally, m may be 0–30 for use in the liquid phase reaction 0–200 for use in the solid phase reaction.

Clearly, according to this invention, oligodeoxynucleotides of various chain lengths may be prepared as desired according to reaction (10) by varying the values of n and m in the starting compounds of general formulae (I) and (XXV). In cases where oligodeoxynucleotides of general formula (XXIV) with relatively long chain lengths are desired, the oligodeoxynucleotide-forming reaction (10) may be effected by modifying it to use a compound of general formula (XXXIV) in place of that of general formula (XXV).

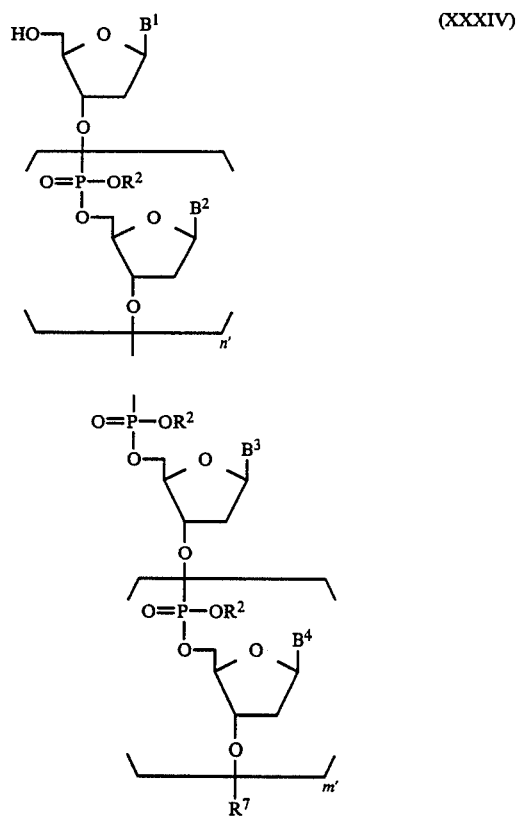

(XXXIV)

wherein $R^2$, $R^7$, $B^1$, $B^2$, $B^3$ and $B^4$ have the meanings as defined above and n' and m' each are a positive integer. Compounds of general formula (XXXIV) may be easily derived from compounds of general formula (XXIV) prepared according to reaction (10) of this invention by selectively removing hydroxy-protecting group $R^1$ of compounds (XXIV) in a known manner. Thus, in cases where group $R^1$ is a triarylmethyl group such as dimethoxytrityl or monomethoxytrityl group, there may often be used for this purpose a protonic acid such as benzenesulfonic acid, dichloroacetic acid and trichloroacetic acid and a Lewis acid such as zinc bromide.

If compound (XXXIV) is prepared in the liquid phase reaction as above-mentioned, the compound may usually be isolated and purified by, for example, silica gel chromatography before reuse in said reaction (10). On the other hand, if compound (XXXIV) is prepared in such solid phase reaction as above-mentioned, it is impossible to isolate and purify the compound. In such cases, care must be taken to preserve the presence of a free hydroxyl group on the 5'-position of compound (XXV). Thus, it is necessary, before the removal of $R^1$ of compound (XXIV) to give compound (XXXIV), to cap the 5'—OH group of compound (XXV) by any suitable method. The capping reaction may fundamentally be one capable of forming a stable chemical bond with the 5'-OH group of compound (XXV). Most often, the esterification reaction using acetic anhydride-base (pyridine or a combination of 2,6-dimethylpyridine and 4-dimethylaminopyridine) system may be used.

EXAMPLES

Figure 1:
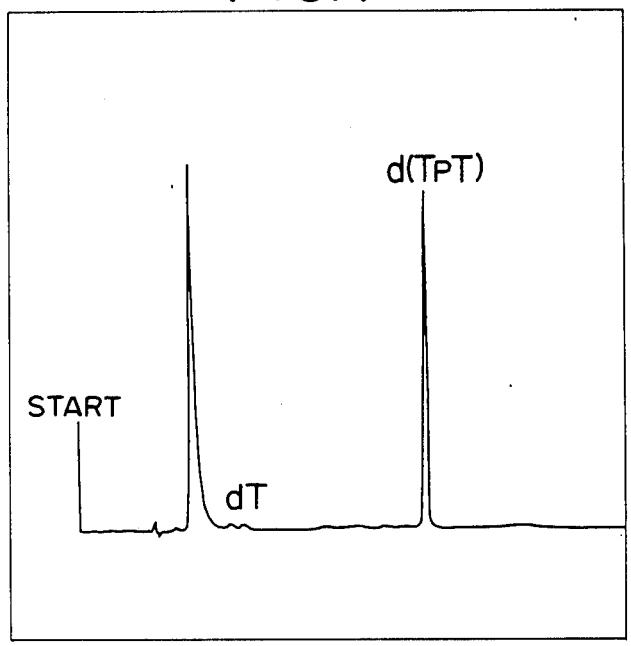
FIGS. 1, 2, 3 and 4 are elution curves of deprotected products of the final object compounds, oligodeoxynucleotides, of this invention prepared in Examples 19, 20, 21 and 22, respectively. In these figures, dT is thymidine, d(TpT) is thymidine dimer, d(CpT) is dimer of deoxycytidine-thymidine, dApT is dimer of deoxyadenosinethymidine and $d(Tp)_8T$ is thymidine nonamer.

The following Examples further illustrate, but not limit, this invention, in which Examples 1 to 9 illustrate the preparation of deoxynucleosido-phosphorsulfides of general formula (I) when n=0, i.e. general formula (IA); Examples 10 to 13 illustrate the preparation of deoxynucleotido-phosphorsulfides of general formula (I) where n=1, i.e. general formula (IB); and Examples 14 to 22 illustrate the preparation of oligodeoxynucleotides of general formula (XXIV). Further, the preparation of 1,2,4-triazolylphosphine compounds of general formula (XXVI) is illustrated by Reference Examples 1 to 5 and the preparation of trialkylstannyl azole compounds of general formula (XXVII) is illustrated by Reference Examples 6 to 8.

In all the Examples and Reference Examples, the following abbreviations are used.

Et: ethyl group; n-Pr: n-propyl group; i-Pr: i-propyl group; n-Bu: n-butyl group;

Bz: benzoyl group;

MMTr: monomethoxytrityl group;

DMTr: dimethoxytrityl group;

TBDMS: t-butyldimethylsilyl group;

T: thymine residue

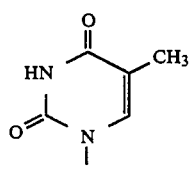

$C^{bz}$: $N^4$-benzoylcytosine residue

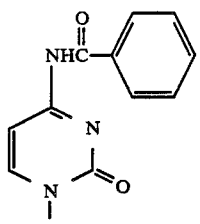

A$^{pht}$: N$^6$-phthaloyladenine residue

G$_{pro}$$^{DPC}$: O$^6$-diphenylcarbamoyl-N$^2$-propionylguanine residue

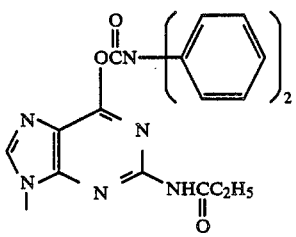

A$^{bz}$: N$^6$-benzoyladenine residue

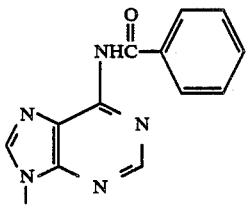

G$^{ib}$: N$^2$-i-butylylguanine residue

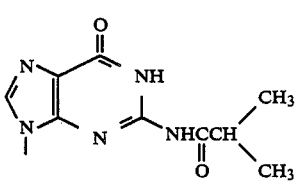

EXAMPLE 1

Preparation of 5'-O-dimethoxytritylthymidine-3'-O-(2-chlorophenyloxy-2-methylphenylthio)phosphine

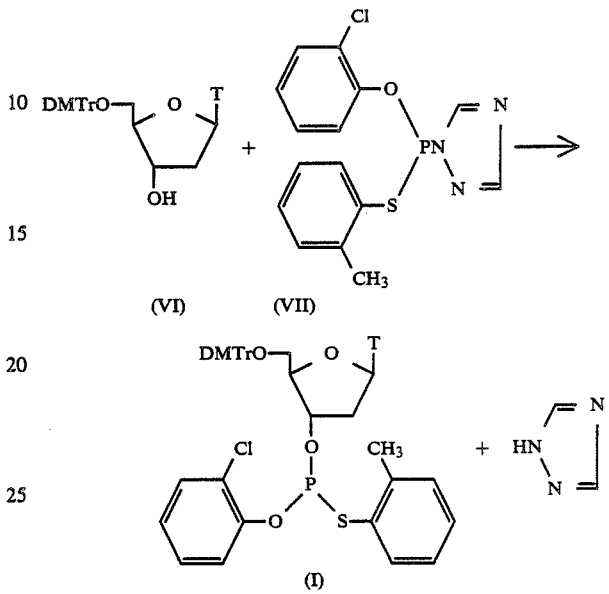

A solution of 2-chlorophenyloxy-2-methylphenylthio-1,2,4-triazolylphosphine (VII) in deuterochloroform (1 ml) which was prepared in Reference Example 1 hereinafter given was slowly added to a suspension of 5'-O-dimethoxytritylthymidine (VI) (0.163 g, 0.3 mmol.) in deuterochloroform (0.5 ml) at 0° C. After the addition, the temperature of the resulting mixture raised to room temperature and stirred for 1.5 hours at that temperature. Rf values and the $^1$HNMR spectrum of the solution thus obtained were measured as follows:

R$_f$(CHCl$_3$:MeOH=80:1)=0.30

$^1$HNMR (CDCl$_3$, TMS)δ; 1.46 (s, 3H, 5-CH$_3$), 2.20–2.85 (m, 5H, with a singlet at 2.28 and 2.38 ppm, 2' and CH$_3$C$_6$H$_4$S—), 3.35–3.65 (m, 2H, 5'), 3.69 (s, 3H, CH$_3$OC$_6$H$_4$—), 3.70 (s, 3H, CH$_3$OC$_6$H$_4$—), 4.25–4.50 (m, 1H, 4'), 5.45–5.80 (m, 1H, 3'), 6.49 (t, 1H, J=7.0 Hz, 1'), 6.65–6.90 (m, 4H, ph), 6.90–7.75 (m, 18H, ph and 6), 8.16 (s, 2H, HNC$_2$H$_2$N$_2$), 10.3 (s, 1H, NH), 12.8 (s, 1H, HNC$_2$H$_2$N$_2$) ppm.

Then, chloroform (50 ml) was added to this solution and the chloroform solution was washed with a saturated aqueous sodium chloride solution and dried over anhydrous sodium sulfate. Most of the chloroform was distilled off in vacuo and the residue (about 2 ml) was added dropwise to a stirred n-pentane (200 ml) at 0° C., resulting in the immediate deposition of white powder. After continuing the stirring at that condition for 30 minutes, the powder was recovered by filtration and dried in vacuo at room temperature for 8 hours, affording the title compound (I) (0.235 g; yield 95%).

Rf(CHCl$_3$:MeOH=80:1)=0.30

EXAMPLES 2-9

Various deoxynucleosides (VI) and 1,2,4-triazolylphosphine compounds (VII) shown in Table 1 were reacted in deuterochloroform in such molar ratio and for such reaction time as shown in Table 1 in the same manner as in Example 1 and the resulting reaction mixture was aftertreated in the same manner as in Example 1 to afford various deoxynucleoside phosphorsulfide compounds (I) as shown in Table 1.

TABLE 1

| Example No. | Reactants | | Mole ratio (VII)/(VI) | Reaction time (min) | Yield (%) | Product Deoxynucleoside phosphorsulfide compound (I) | | |
|---|---|---|---|---|---|---|---|---|
| | Deoxynucleoside (VI) | 1,2,4-Triazolyl-phosphine compound (VII) | | | | Structural formula | Rf(CHCl₃: MeOH = 80:1) | ¹HNMR(CDCl₃,TMS): δ(ppm) |
| 2 | [DMTrO-sugar-T with OH] | [CH₃O, triazolyl-P-S-(2-methylphenyl)] | 2.0 | 120 | 93 | [DMTrO-sugar-T, O-P(OCH₃)-S-(2-methylphenyl)] | 0.21 | 1.48(s,3H,5-CH₃), 2.10–2.80(m,5H,with a singlet at 2.58 ppm,2′ and CH₃C₆H₄S—), 3.20–3.70(m,5H,with a doublet at 3.59 and 3.63 ppm, J=10.0Hz,5′ and CH₃O—), 3.72(s,3H,CH₃OC₆H₄—), 3.74(s,3H,CH₃OC₆H₄O—), 4.10–4.35(m,1H,4′), 4.90–5.25(m,1H,3′), 6.44(t,1H,J=7.0Hz,1′), 6.65–6.90(m,4H,ph), 6.90–7.75(m,14H,ph and 6), 10.4(s,1H,NH). |
| 3 | [DMTrO-sugar-T with OH] | [2-Cl-phenoxy, triazolyl-P-S-(2,6-dimethylphenyl)] | 1.2 | 30 | 94 | [DMTrO-sugar-T, O-P(O-2-Cl-phenyl)-S-(2,6-dimethylphenyl)] | 0.30 | 1.45(s,3H,5-CH₃), 2.20–2.85(m,8H,with a singlet at 2.26 and 2.36 ppm,2′ and (CH₃)₂O₆H₃S—), 3.35–3.65(m,2H,5′), 3.71(s,3H,CH₃OC₆H₄—), 3.73(s,3H,CH₃OC₆H₄—), 4.25–4.50 (m,1H,4′), 5.40–5.75(m,1H,3′), 6.50(t,1H,J=7.0Hz,1′), 6.65–7.55(m,20H,ph), 7.66(s,1H,6), 10.2(s,1H,NH). |
| 4 | [DMTrO-sugar-C^bz with OH] | [2-Cl-phenoxy, triazolyl-P-S-(2-methylphenyl)] | 1.2 | 30 | 95 | [DMTrO-sugar-C^bz, O-P(O-2-Cl-phenyl)-S-(2-methylphenyl)] | 0.48 | 2.20–2.70(m,4H,with a singlet at 2.29 and 2.36 ppm,0.5×2′ and CH₃C₆H₄S—), 2.80–3.10(m,1H,0.5×2′), 3.40–3.90(m,8H,with a singlet at 3.65 and 3.69 ppm,5′ and 2×CH₃OC₆H₄—), 4.30–4.60(m,1H,4′), 5.40–5.70 (m,1H,3′), 6.36(t,1H,J=7.0Hz,1′), 6.65–7.70(m,26H,ph), 7.80–8.00(m,1H,5), 8.10–8.30 (m,1H,6), 10.6(s,1H,NH). |

TABLE 1-continued

| | Reactants | | | | | Product | | |
|---|---|---|---|---|---|---|---|---|
| Example No. | Deoxynucleoside (VI) | 1,2,4-Triazolyl-phosphine compound (VII) | Mole ratio (VII)/(VI) | Reaction time (min) | Yield (%) | Deoxynucleoside phosphorsulfide compound (I) | | |
| | | | | | | Structural formula | Rf(CHCl$_3$: MeOH = 80:1) | $^1$HNMR(CDCl$_3$,TMS): δ(ppm) |
| 5 | DMTrO—[A$^{pht}$ deoxyribose with OH] | [triazolyl phosphine with 2-Cl-C$_6$H$_4$O and 2-CH$_3$-C$_6$H$_4$S] | 1.3 | 60 | 95 | DMTrO—[A$^{pht}$ deoxyribose]—O—P(S-2-CH$_3$C$_6$H$_4$)(O-2-ClC$_6$H$_4$) | 0.70 | 2.34(s,1.5H,0.5×CH$_3$C$_6$H$_4$S—), 2.41(s,1.5H,0.5×CH$_3$C$_6$H$_4$S—), 2.55–3.25(m,2H,2'), 3.35–3.65 (m,2H,5'), 3.70(s,6H,2× CH$_3$OC$_6$H$_4$—), 4.30–4.75(m,1H, 4'), 5.45–5.85(m,1H,3'), 6.45–7.60(m,18H,1' and ph), 7.60–8.05(m,4H,ph), 8.35 (s,1H,2), 8.93(s,1H,8). |
| 6 | MMTrO—[G$^{DPC}_{pro}$ deoxyribose with OH] | [triazolyl phosphine with 2-Cl-C$_6$H$_4$O and 2-CH$_3$-C$_6$H$_4$S] | 1.3 | 20 | 94 | MMTrO—[G$^{DPC}_{pro}$ deoxyribose]—O—P(S-2-CH$_3$C$_6$H$_4$)(O-2-ClC$_6$H$_4$) | 0.60 | 1.14(t,1.5H,J=7.0Hz, 0.5×CH$_3$CH$_2$—), 1.16(t, 1.5H,J=7.0Hz,0.5×CH$_3$CH$_2$—), 2.28(s,1.5H,0.5×CH$_3$C$_6$H$_4$S—), 2.37(s,1.5H,0.5×CH$_3$C$_6$H$_4$S—), 2.40–3.20(m,4H,with a quadruplet at 2.55 and 2.57 ppm J=7.0Hz,2' and CH$_3$CH$_2$—), 3.25–3.70(m,2H,5'), 3.64(s,3H, CH$_3$OC$_6$H$_4$—), 4.30–4.65(m,1H, 4'), 5.45–5.80(m,1H,3'), 6.41(t,1H,J=7.0Hz,1'), 6.55–6.85(m,2H,ph), 6.85–7.65(m, 30H,ph), 8.11(s,1H,8), 8.53 (s,0.5H,0.5×NH), 8.56(s, 0.5H,0.5×NH). |
| 7 | DMTrO—[T deoxyribose with OH] | CH$_2$=CH—CH$_2$O—[triazolyl phosphine with 2-CH$_3$-C$_6$H$_4$S] | 2.0 | 30 | 75 | DMTrO—[T deoxyribose]—O—P(S-2-CH$_3$C$_6$H$_4$)(OCH$_2$—CH=CH$_2$) | 0.80 | 1.42(s,3H,5-CH$_3$), 2.05–2.70 (m,5H,with a singlet at 2.37 and 2.38 ppm,2' and o-CH$_3$C$_6$H$_4$S—), 3.25–3.60(m, 2H,5'), 3.73(s,3H,CH$_3$OC$_6$H$_4$—), 4.00–4.70(m,3H,4' and CH$_2$=CH—CH$_2$O—), 4.85–5.45(m,3H,3' and CH$_2$=CH—CH$_2$O—), 5.55–6.15(m,1H, CH$_2$=CH—CH$_2$O—), 6.20–6.55(m,1H, 3'), 6.65–6.90(m,4H,ph), 6.90–7.70(m,14H,ph and 6), 8.50(s,1H,NH). |

TABLE 1-continued

| Example No. | Reactants | | Mole ratio (VII)/(VI) | Reaction time (min) | Yield (%) | Product Deoxynucleoside phosphorsulfide compound (I) | | |
|---|---|---|---|---|---|---|---|---|
| | Deoxynucleoside (VI) | 1,2,4-Triazolyl-phosphine compound (VII) | | | | Structural formula | Rf(CHCl₃: MeOH = 80:1) | ¹HNMR(CDCl₃,TMS): δ(ppm) |
| 8 | 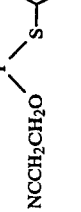 |  | 2.0 | 90 | 71 |  | 0.42 | 1.45(s,3H,5-CH₃), 2.10–2.85(m,7H,with a singlet at 2.38 ppm,2',o-CH₃C₆H₄S— and NCCH₂CH₂O—), 3.25–3.60 (m,2H,5'), 3.74(s,3H,CH₃OC₆H₄—), 3.76(s,3H,CH₃OC₆H₄—), 3.85–4.35(m,3H,4' and NCCH₂CH₂O—), 4.85–5.25(m,1H, 3'), 6.38(t,1H,J=7.0Hz,1'), 6.65–6.90(m,4H,ph), 6.90–7.45(m,13H,ph), 7.52(s,1H,6), 8.96(s,1H,NH). |
| 9 |  | 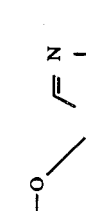 | 1.3 | 60 | 85 |  | 0.34 | 2.31(s,1.5H,0.5×CH₃C₆H₄S—), 2.37(s,1.5H,0.5×CH₃C₆H₄S—), 2.55–3.25(m,2H,2'), 3.25–3.60 (m,2H,5'), 3.70(s,6H,2×CH₃OC₆H₄—), 4.35–4.65(m,1H,4'), 5.45–5.75(m,1H,3'), 6.30–6.85(m,5H,1' and ph), 6.85–7.60(m,20H,ph), 7.75–8.05 (m,2H,ph), 8.05–8.20(m,1H,2), 8.55–8.75(m,1H,8), 8.88(s,1H,NH)ppm. |

EXAMPLE 10

Preparation of P-2-chlorophenyl-5'-O-dimethoxythymidyl-3'-O-[(2-chlorophenyloxy-2-methylphenylthio)phosphino]-(3'→5')thymidine

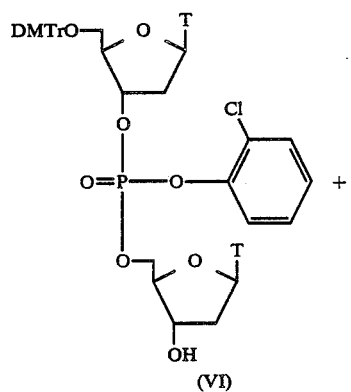

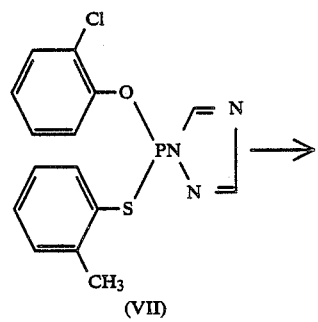

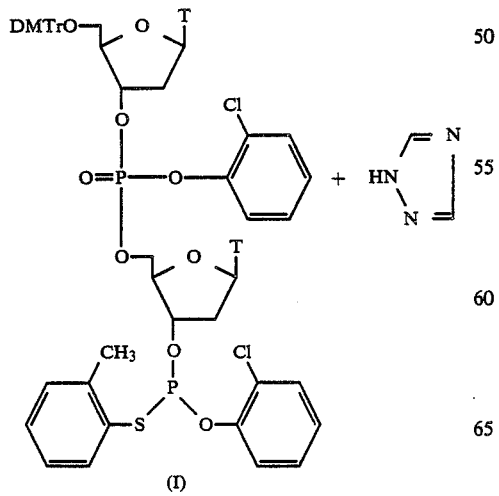

To a solution of P-2-chlorophenyl-5'-O-dimethoxytritylthymidyl-(3'→5')-thymidine (VI) (0.480 g; 0.5 mmol.) in chloroform (1.5 ml) was added at 0° C. a chloroform solution (1 ml) of 2-chlorophenyloxy-2-methylphenylthio-1,2,4-triazolylphosphine (VII) which was prepared by reacting 2-chlorophenyloxy-2-methylphenylthiochlorophosphine (0.222 g; 0.7 mmol.) with trimethylsilyl-1,2,4-triazole (0.104 g; 0.735 mmol.) in the same manner as in Reference Example 1. The resulting mixture was restored to room temperature and stirred at that temperature for 1 hour, upon which a thin layer chromatography (TLC) of the reaction solution confirmed that the spot of the starting compound (VI) (Rf=0.29; CHCl$_3$:MeOH=20:1) had disappeared. Then, chloroform (100 ml) was added to the reaction solution and the chloroform layer separated was washed with a saturated aqueous sodium chloride solution (50 ml×3) and then dried over anhydrous magnesium sulfate. Most of the chloroform was distilled off in vacuo and the residue (about 2 ml) was added dropwise to a stirred n-pentane (300 ml) at 0° C., resulting in the immediate deposition of white powder. After continuing the stirring for 30 minutes, the powder was recovered by filtration and dried in vacuo at room temperature for 8 hours, yielding the titled compound (1.054 g; yield 85%).

Rf (CHCl$_3$:MeOH=20:1)=0.56

$^1$HNMR (CDCl$_3$, TMS)δ; 1.35 (s, 3H, 5—CH$_3$), 1.84 (s, 3H, 5—CH$_3$), 1.90–2.85 (m, 7H, with a singlet at 2.34, o—CH$_3$C$_6$H$_4$S— and 2×2'), 2.85–3.65 (m, 2H, 5'), 3.73 (s, 6H, 2×CH$_3$OC$_6$H$_4$—), 3.95–4.70 (m, 4H, 2×4' and 5'), 5.05–5.65 (m, 2H, 2×3'), 6.05–6.55 (m, 2H, 2×1'), 6.60–6.85 (m, 4H, ph), 6.85–7.60 (m, 23H, ph and 2×6), 9.28 (s, 1H, NH), 9.36 (s, 1H, NH) ppm.

EXAMPLES 11–13

Various dideoxynucleotides (VI) shown in Table 2-A were reacted with 2-chlorophenyloxy-2-methylphenylthio-1,2,4-triazolylphosphine (VII) in chloroform in such molar ratio and for such reaction time as shown also in Table 2-A and the resulting reaction mixture was worked up in the same manner as in Example 10 to yield various deoxynucleotide phosphorsulfide compounds (I) as shown in Table 2-B.

TABLE 2-A
| Example No. | Reactants Deoxynucleotide (VI) | 1,2,4-Triazolylphosphine compound (VII) | Mole ratio (VII)/(VI) | Reaction time (min) |
|---|---|---|---|---|
| 11 | 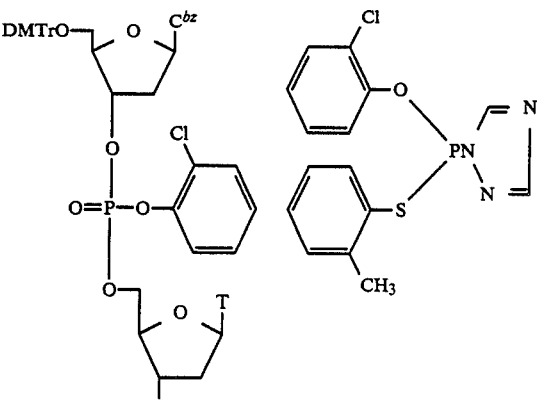 | 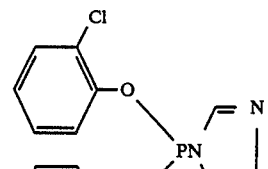 | 2.0 | 120 |
| 12 | 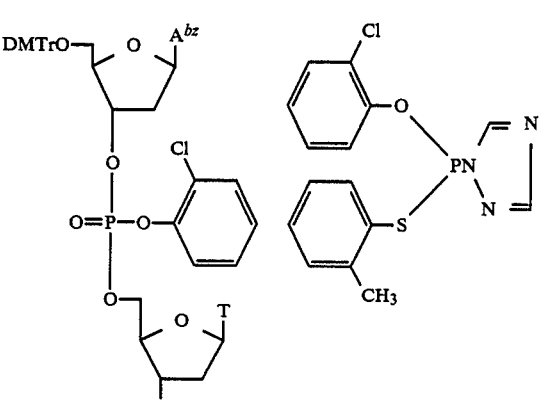 | 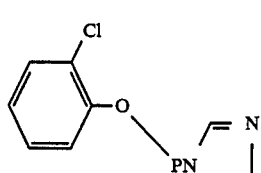 | 1.5 | 60 |
| 13 | 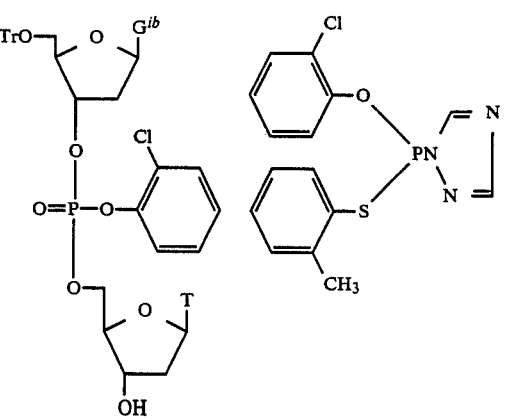 | 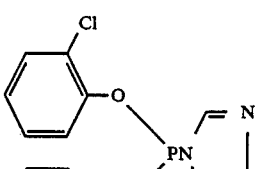 | 1.5 | 60 |

TABLE 2-B

Product
Deoxynucleotide phosphorsulfide compound (I)

| Example No. | Yield (%) | Structural formula | $R_f$(CHCl$_3$: MeOH = 20:1) | $^1$HNMR(CDCl$_3$,TMS): δ(ppm) |
|---|---|---|---|---|
| 11 | 71 | [structure with DMTrO, C$^{bz}$, CH$_3$, Cl, P=O, S, P] | 0.65 | 1.82(s,3H,5-C$\underline{H}_3$), 1.90–3.15(m,7H,with a singlet at 2.34,o-C$\underline{H}_3$C$_6$H$_4$S— and 2×2'), 3.15–3.55(m,2$\underline{H}$,5'), 3.72(s, 6H,2×C$\underline{H}_3$OC$_6$H$_4$—), 3.95–4.65(m,4H, 2×4' and 5'), 5.05–5.65(m,2H,2×3'), 6.05–6.45(m,2H,2×1'), 6.60–6.85(m, 4H,ph), 6.85–7.65(m,26H,ph), 7.70–8.10 (m,3H,5 and 2×6), 8.60–9.30(m,2H,2×N$\underline{H}$). |
| 12 | 75 | [structure with DMTrO, A$^{bz}$, CH$_3$, Cl, P=O, S, P] | 0.75 | 1.82(s,3H,5-C$\underline{H}_3$), 1.95–3.25(m,7H,with a singlet at 2.34,o-C$\underline{H}_3$C$_6$H$_4$S— and 2×2'), 3.25–3.55(m,2$\underline{H}$,5'), 3.70(s, 6H,2×C$\underline{H}_3$OC$_6$H$_4$—), 4.05–4.75(m,4H, 2×4' and 5'), 5.15–5.65(m,2H, 2×3'), 5.95–6.55(m,2H,2×1'), 6.60–6.85(m,4H,ph), 6.85–7.60(m,26H, ph), 7.75–8.15(m,3H,2,6 and 8), 8.35– 8.65(m,1H,N$\underline{H}$), 9.10–10.3(m,1H,N$\underline{H}$). |
| 13 | 70 | [structure with MMTrO, G$^{ib}$, CH$_3$, Cl, P=O, S, P] | 0.60 | 0.80–1.30(m,6H,(C$\underline{H}_3$)$_2$CH—), 1.65–2.05 (m,3H,5-C$\underline{H}_3$), 2.33(s,3H,o-C$\underline{H}_3$C$_6$H$_4$S—), 2.15–3.00(m,5H,2×2' and Me$_2$C$\underline{H}$—), 3.05–3.45(m,2H,5'), 3.70(s,3H, C$\underline{H}_3$OC$_6$H$_4$—), 3.95–4.75(m,4H,2×4' and 5'), 5.05–5.65(m,2H,2×3'), 6.00– 6.45(m,2H,2×1'), 6.60–6.85(m,2H,ph), 6.85–7.75(m,26H,ph,6 and 8), 9.60– 10.4(m,2H,2×N$\underline{H}$), 11.8–12.2(m,1H,N$\underline{H}$). |

EXAMPLE 14

Preparation of
P-2-chlorophenyl-5'-O-dimethoxytritylthymidyl-(3'→5')-3'-O-benzoylthymidine

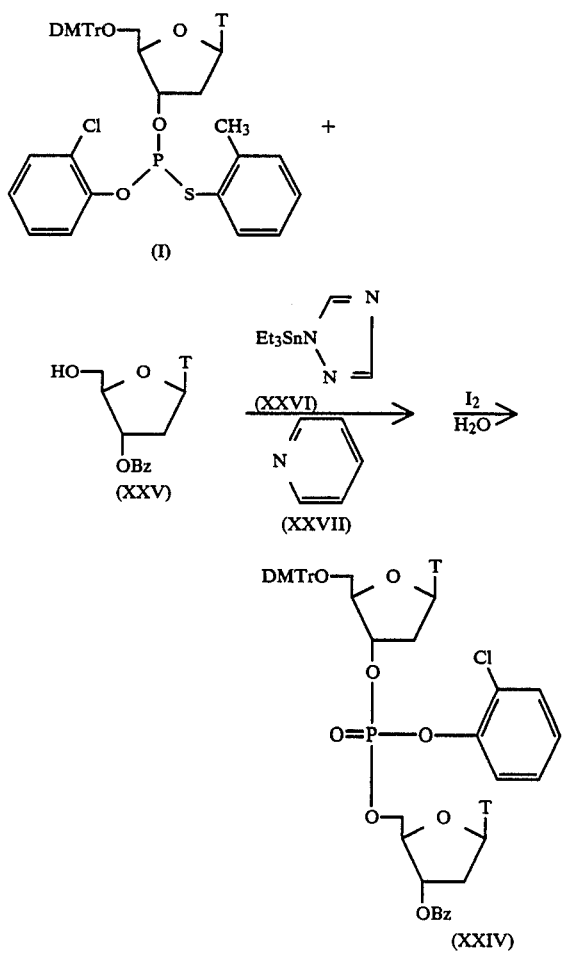

5'-O-Dimethoxytritylthymidine-3'-O-(2-chlorophenyloxy-2-methylphenylthio)phosphine (I) (5.78 g; 7 mmol.), triethylstannyl-1,2,4-triazole (XXVI) (4.11 g; 15 mmol.) and 1,2-dichloroethane (50 ml) were added succesively to 3'-O-benzoylthymidine (XXV) (1.73 g; 5 mmol.). Immediately thereafter, pyridine (4.0 ml; 50 mmol.) was also added and the resulting mixture was stirred at room temperature for 5 minutes. Then, a solution of iodine (6.35 g, 25 mmol.) in a mixture of tetrahydrofuran (100 ml), pyridine (5.5 ml) and water (5.5 ml) was added to the stirred mixture and the stirring was continued for further 1 minute at room temperature. The reaction mixture was washed with a saturated aqueous sodium hydrogen carbonate solution (50 ml×3) and dried over anhydrous magnesium sulfate. After filtration, the filtrate was concentrated in vacuo and the residue was subjected to silica gel column chromatography using a mixture of chloroform-methanol (10:1) as eluent. The eluate was concentrated to dryness to leave a foamed solid which was then dried in vacuo to afford the titled compound (4.84 g; yield 91%).

Rf(CHCl$_3$:MeOH=10:1)=0.57

$^1$HNMR (CDCl$_3$, TMS); δ 1.40 (s, 3H, 5—CH$_3$), 1.82 (s, 3H, 5—CH$_3$), 2.10–2.90 (m, 4H, 2×2'), 3.10–3.65 (m, 2H, 5'), 3.66 (s, 6H, 2×CH$_3$O—), 4.05–4.70 (m, 4H, 2×4' and 5'), 5.20–5.60 (m, 2H, 2×3'), 6.38 (t, 2H, J=7.0 Hz, 2×1'), 6.60–6.90 (m, 4H, ph), 6.90–8.00 (m, 20H, 2×6 and ph) and 9.88 (s, 2H, NH) ppm.

EXAMPLES 15–18

In each of these Examples, the procedure of Example 14 was repeated except that deoxynucleoside- or deoxynucleotide-phosphorsulfide compound (I), trialkylstannyl azole compound (XXVI), base (XXVII) and deoxynucleoside compound (XXV) used were as shown in Table 3-A. The results are given in Table 3-B.

TABLE 3-A

| Example No. | Deoxynucleoside- or deoxynucleotide-phosphorsulfide compound (I) | Trialkylstannyl azole compound (XXVI) | Base (XXVII) | Deoxynucleoside compound (XXV) | Reaction time (min) |
|---|---|---|---|---|---|
| 15 | DMTrO-thymidine-3'-O-P(2-Cl-phenoxy)(2-CH$_3$-phenylthio) | n-Pr$_3$SnN-benzotriazole | 2-methylpyridine | HO-deoxyribose-C$^{bz}$-OTBDMS | 5 |
| 16 | DMTrO-thymidine-3'-O-P(2-Cl-phenoxy)(2-CH$_3$-phenylthio) | n-Bu$_3$SnN-1,2,4-triazole | N-methyl-1,2,4-triazole | HO-deoxyribose-A$^{bz}$-OBz | 5 |

TABLE 3-A-continued

| Example No. | Reactants | | | | Reaction time (min) |
|---|---|---|---|---|---|
| | Deoxynucleoside- or deoxynucleotide-phosphorsulfide compound (I) | Trialkylstannyl azole compound (XXVI) | Base (XXVII) | Deoxynucleoside compound (XXV) | |
| 17 | [structure: DMTrO–sugar–T with phosphite bearing O-(2-Cl-phenyl) and S-(2-methylphenyl)] | n-Bu$_3$SnN(triazole) | 2,6-lutidine (2,6-dimethylpyridine) | [structure: HO–sugar–G$^{ib}$, OBz] | 5 |
| 18 | [structure: DMTrO–sugar–T with 3'-O–P(=O)(O-2-Cl-phenyl)(CH$_3$)] | n-Pr$_3$SnN(benzotriazole) | N-methylimidazole | [structure: HO–sugar–T, OTBDMS] | 5 |
| | [structure: DMTrO–sugar–T with phosphite bearing O-(2-Cl-phenyl), S-(2-Cl-phenyl), O-(2-methylphenyl)] | | | | |

TABLE 3-B

| Example No. | Product Dideoxynucleotide or trideoxynucleotide | | | |
|---|---|---|---|---|
| | Structural formula | Yield (%) | Rf(CHCl$_3$:MeOH = 10:1) | $^1$HNMR (CDCl$_3$, TMS); δ(ppm) |
| 15 | [structure: DMTrO–sugar–T, 3'-O–P(=O)(O-2-Cl-phenyl)–O–sugar–C$^{bz}$, OTBDMS] | 87 | 0.64 | 0.06(s,6H,(CH$_3$)$_2$Si—), 0.95(s,9H, (CH$_3$)$_3$Si—), 1.38(s,3H,5-CH$_3$), 1.90–2.85(m,4H,2 × 2'), 3.20–3.60(m,2H, 5'), 3.70(s,6H,2 × CH$_3$O—), 3.90–4.55(m,5H,3',2 × 4' and 5'), 5.20–5.40(m,1H,3'), 6.15(t,1H,J=7.0Hz, 1'), 6.36(t,1H,J=7.0Hz,1'), 6.65–6.90(m,4H,ph), 6.95–7.65(m,17H,6 and ph), 7.70–7.90(m,2H,ph), 7.96 (d,1H,J=7.0Hz,5), 8.52(d,1H,J=7.0Hz, 6), 8.94(bs,1H,NH), 9.47(s,1H,NH). |

TABLE 3-B-continued

| Example No. | Structural formula | Product Dideoxynucleotide or trideoxynucleotide Yield (%) | Rf(CHCl₃:MeOH = 10:1) | ¹HNMR (CDCl₃, TMS); δ(ppm) |
|---|---|---|---|---|
| 16 | [Structure: DMTrO-sugar-T, phosphate linked to 2-chlorophenyl, connected to sugar-A^bz with OBz] | 86 | 0.59 | 1.28(s,1.5H,0.5 × 5-C$H_3$), 1.30(s, 1.5H,0.5 × 5-C$H_3$), 2.20–3.40(m,6H, 2 × 2' and 5'), 3.60(s,6H,2 × C$H_3$O—), 4.00–4.60(m,4H,2 × 4' and 5'), 5.10–5.40(m,1H,3'), 5.50–5.80 (m,1H,3'), 6.10–6.60(m,2H,2 × 1'), 6.60–6.80(m,4H,ph), 6.80–7.60(m, 20H,6 and ph), 7.80–8.10(m,4H,ph), 8.22(s,0.5H,0.5 × 2), 8.28(s,0.5H, 0.5 × 2), 8.68(s,1H,8), 9.86(s,1H, N$H$), 10.40(s,0.5H,0.5 × N$H$), 10.68 (s,0.5H,0.5 × N$H$). |
| 17 | [Structure: DMTrO-sugar-T, phosphate linked to 2-chlorophenyl, connected to sugar-G^ib with OBz] | 84 | 0.47 0.52 | 0.80–1.25(m,6H,(C$H_3$)₂CH—), 1.36 (s,1.5H,0.5 × 5-C$H_3$), 1.38(s,1.5H, 0.5 × 5-C$H_3$), 2.20–3.60(m,7H, 2 × 2', 5 and Me₂C$H$—), 3.65(s, 6H,2 × C$H_3$O—), 4.00–4.90(m,4H, 2 × 4' and 5'), 5.05–5.30(m,1H,3'), 5.30–5.65(m,1H,3'), 6.05–6.50(m, 2H,2 × 1'), 6.60–6.85(m,4H,ph), 6.85–7.55(m,17H,6 and ph), 7.60 (s,0.5H,0.5 × 8), 7.66(s,0.5H, 0.5 × 8), 7.80–8.00(m,2H,ph), 9.58 (s,1H,N$H$), 9.98(s,0.5H,0.5 × N$H$), 10.36(s,0.5H,0.5 × N$H$), 11.84(s, 0.5H,0.5 × N$H$), 12.06(s,0.5H,0.5 × N$H$). |
| 18 | [Structure: DMTrO-sugar-T, phosphate linked to 2-chlorophenyl, connected to sugar-T, phosphate linked to 2-chlorophenyl, connected to sugar-T with OTBDMS] | 90 | 0.78 | 0.06(s,6H,(C$H_3$)₂Si—), 0.94(s,9H, (C$H_3$)₃Si—), 1.37(s,3H,5-C$H_3$), 1.70– 2.00(m,6H,2 × 5-C$H_3$), 2.00–2.80 (m,6H,3 × 2'), 3.05–3.50(m,2H,5'), 3.70(s,6H,2 × C$H_3$O—), 3.95–4.70 (m,8H,3',3 × 4' and 2 × 5'), 5.10–5.45(m,2H,2 × 3'), 6.05–6.60 (m,3H,3 × 1'), 6.60–6.90(m,4H, ph), 6.90–7.60(m,20H,3 × 6 and ph), 9.72(bs,3H,3 × N$H$). |

The following Examples 19–22 are illustrative of preparation of several oligodeoxynucleotides carried on polystyrene, a polymer-support Ⓟ.

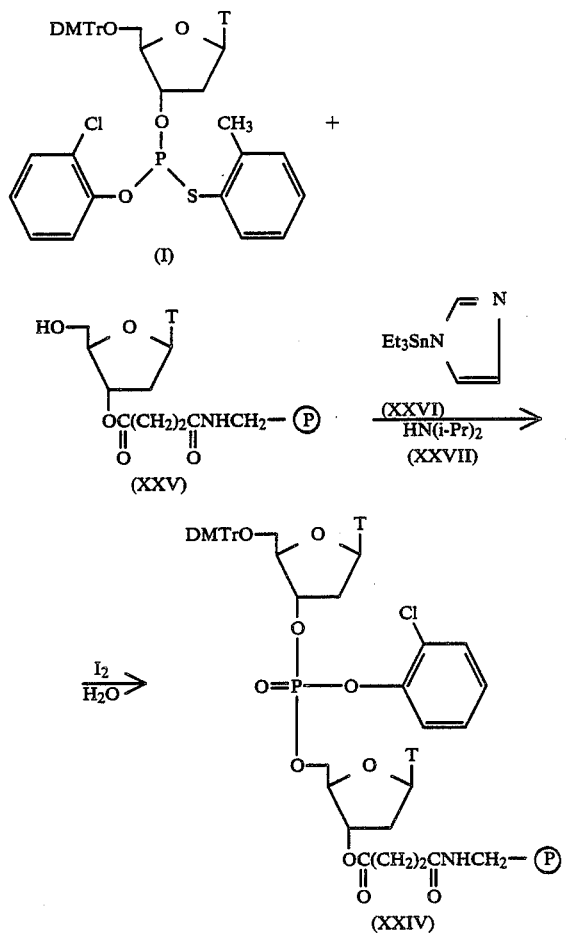

A solution of triethylstannylimidazole (XXVI) (10 mg; 36 μmol.) and diisopropylamine (XXVII) (3.64 mg, 36 μmol.) in 1,2-dichloroethane (0.2 ml) was added to thymidine bound to polystyrene resin (XXV) (10 mg; 1.2 μmol.) which was prepared by reacting 5'-O-dimethoxytritylthymidine attached to polystyrene (Ⓟ) (a commercial product, loading of thymidine, 120 μmol./g of resin) with a 5% trichloroacetic acid solution in 1,2-dichloroethane. Immediately thereafter, there was added to the resulting mixture a solution of 5'-O-dimethoxytritylthymidine-3'-O-(2-chlorophenyloxy-2-methylphenylthio)phosphine (I) (20 mg; 24 μmol.) in 1,2-dichloroethane (0.15 ml). The reaction mixture was shaken at room temperature for 4 minutes and then filtered through a G-4 glass filter to remove the 1,2-dichloroethane and the excess amounts of compounds (I), (XXVI) and (XXVII). The remaining polystyrene resin was washed with methanol (3 ml) and pyridine (3 ml) and then iodine (30 mg, 120 μmol.) in a mixture of tetrahydrofuran/pyridine/water (0.45 ml/0.025 ml/0.025 ml) was added thereto and the resulting mixture was shaken at room temperature for 2 minutes to cause the oxidation reaction. After filtration through a G-4 glass filter to remove the mixture of tetrahydrofuran/pyridine/water containing the excess iodine, the remaining polystyrene resin was washed with pyridine (5 ml×2) and then with 1,2-dichloroethane (5 ml). A small portion of the resin was subjected to a trityl cation test (a test for determining the absorbance at 498 nm; details of this test is, for example, described in H. G. Gassen et al., "Chemical and Enzymatic Synthesis of Gene Fragments" published by Verlag Chemie (Weinheim) in 1982 and references cited therein), which showed that the reaction above proceeded with a yield of 98%. This yield was confirmed by removing the protecting groups on the product therefrom by the method shown below and analyzing the deprotected product by high pressure liquid chromatography (HPLC). That is, to the resin obtained as above was added a solution of syn-4-nitrobenzaldoxime (50 mg. 300 μmol.) and 1,1,3,3-tetramethylguanidine (34.5 mg. 300 μmol.) in a mixture of p-dioxane (0.3 ml) and water (0.3 ml) and the resulting mixture was allowed to stand at room temperature for 10 hours. Then, the reaction mixture was filtered and the filtrate was concentrated. An 80% aqueous acetic acid (1.5 ml) was added to the residue and the mixture was maintained at room temperature for 30 minutes.

Figure 3:
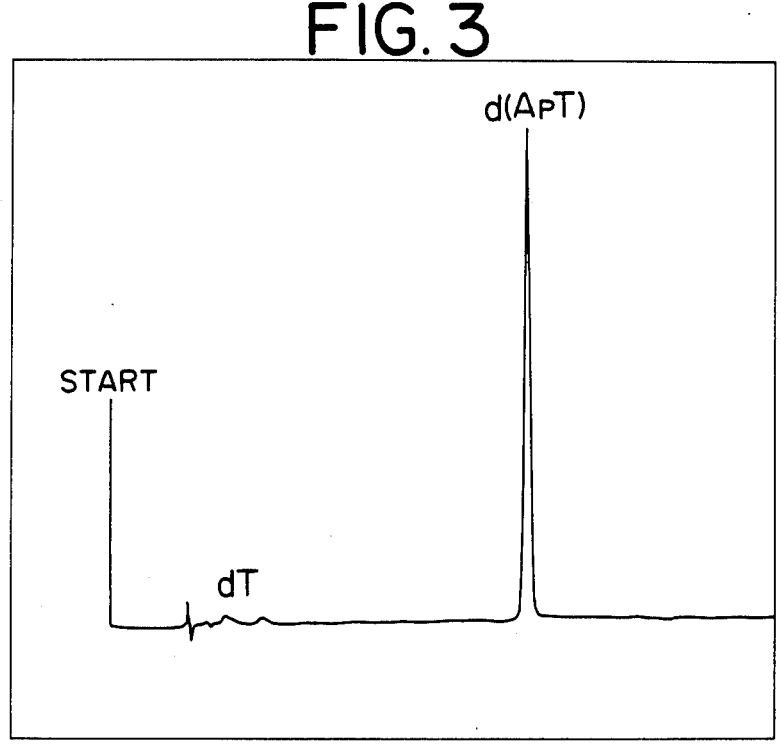
Figure 4:
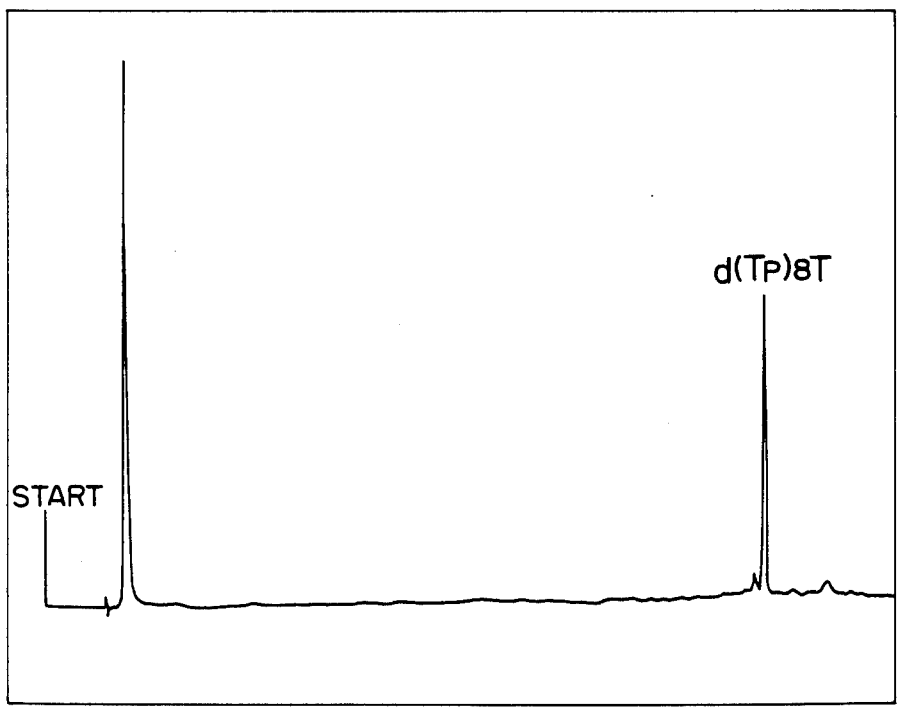

The remaining acetic acid and water were distilled off in vacuo and water (1 ml) and ethyl ether (5 ml) were added to the residue to extract the deprotected product into the aqueous phase. The aqueous layer was washed with ethyl ether (5 ml×4) and then analyzed by HPLC which showed the formation of thymidine dimer (dTpT) and thymidine (dT) in an approximate proportion of 98:2 as shown in FIG. 1 attached hereto. The result shown in FIG. 1 and those shown in FIGS. 2 to 4 hereinafter explained were obtained by using a column of Unisil Pack (Type 5C18-250A manufactured by Gaschro Industry Co., Japan) where the elution was made by gradient elution with 5–25% concentrations of acetonitrile in 0.1M triethylammonium acetate of pH 7.

EXAMPLE 20

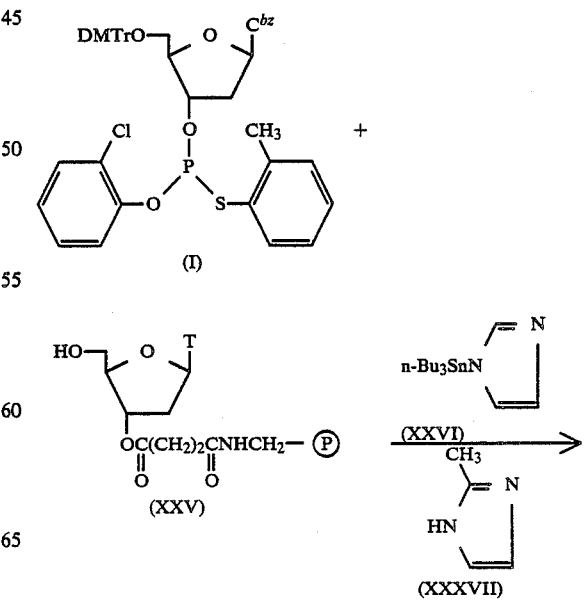

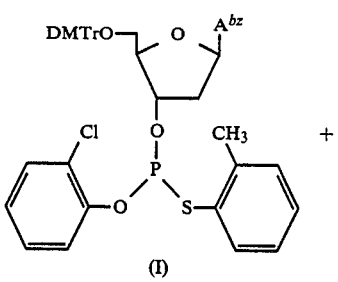

(XXIV)

Figure 2:
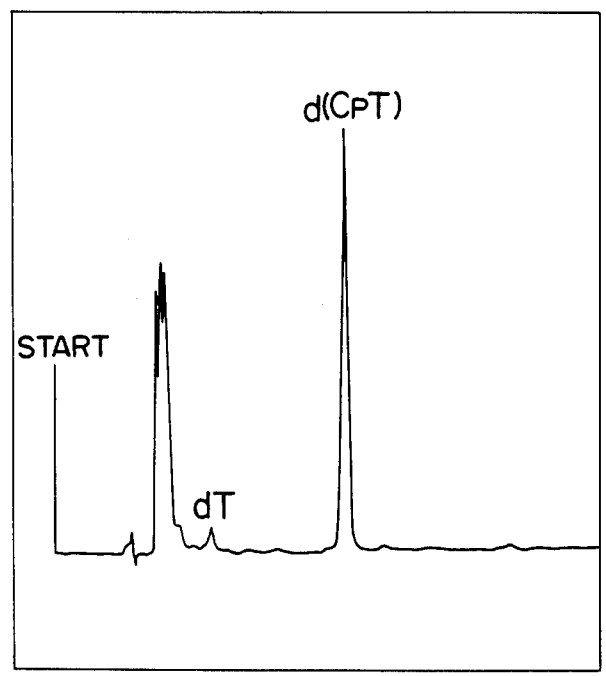

A solution of tri-n-butylstannyl-1,2,4-triazole (XXVI) (34.4 mg; 96 μmol.) and 2-methylimidazole (XXVII) (9.85 mg; 120 μmol.) in 1,2-dichloroethane (0.20 ml) was added to thymidine bound to polystyrene resin (XXV) (10 mg; 1.2 μmol.) which was prepared as described in Example 18. Immediately thereafter, there was added to the resulting mixture a solution of $N^4$-benzoyl-5'-O-dimethoxytrityldeoxycytidine-3'-O-(2-chlorophenyloxy-2-methylphenylthio)phosphine (I) (22 mg; 24 μmol.) in 1,2-dichloroethane (0.15 ml). The reaction mixture was shaken at room temperature for 4 minutes and then filtered through a G-4 glass filter to remove the 1,2-dichloroethane and the excess amounts of compounds (I), (XXVI) and (XXVII). The remaining polystyrene resin was washed with methanol (3 ml) and pyridine (3 ml) and then iodine (30 mg, 120 μmol.) in a mixture of tetrahydrofuran/pyridine/water (0.45 ml/0.025 ml/0.025 ml) was added thereto and the resulting mixture was shaken at room temperature for 2 minutes. After filtration through a G-4 glass filter to remove the mixture of tetrahydrofuran/pyridine/water containing the excess iodine, the remaining polystyrene resin was washed with pyridine (5 ml×2) and then with 1,2-dichloroethane (5 ml). A small portion of the resin mass was subjected to the trityl cation test as in Example 18, which showed the yield of the above reaction to be 98%. This yield was confirmed by removing the protecting groups on the product therefrom by the method shown below and analyzing the deprotected product by high pressure liquid chromatography (HPLC). That is, to the resin mass obtained as above was added a solution of syn-4-nitrobenzaldoxime (50 mg; 300 μmol.) and 1,1,3,3-tetramethylguanidine (34.5 mg; 300 μmol.) in a mixture of p-dioxane (0.3 ml) and water (0.3 ml) and the resulting mixture was allowed to stand at room temperature for 10 hours to conduct the reaction. Then a 28% aqueous ammonia (1 ml) was added to the mixture and the reaction was conducted at 60° C. for 5 hours. The resulting reaction mixture was filtered and the filtrate was concentrated. An 80% aqueous acetic acid (1.5 ml) was added to the residue and the mixture was maintained at room temperature for 30 minutes to cause the reaction. The remaining acetic acid and water were distilled off in vacuo and water (1 ml) and ethyl ether (5 ml) were added to the residue to extract the deprotected product into the aqueous phase. The aqueous layer was washed with ethyl ether (5 ml×4) and then analyzed by HPLC which showed the formation of dimer of deoxycytidine and thymidine [d(CpT), (XXIV')] and thymidine (dT) in an approximate proportion of 98:2 as shown in FIG. 2.

(XXIV')

EXAMPLE 21

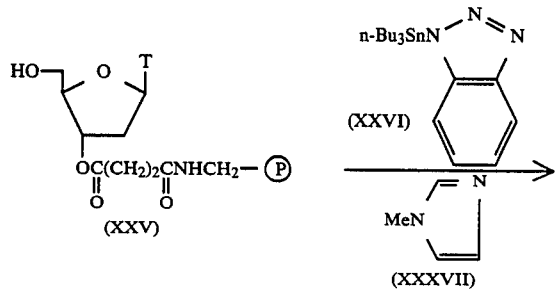

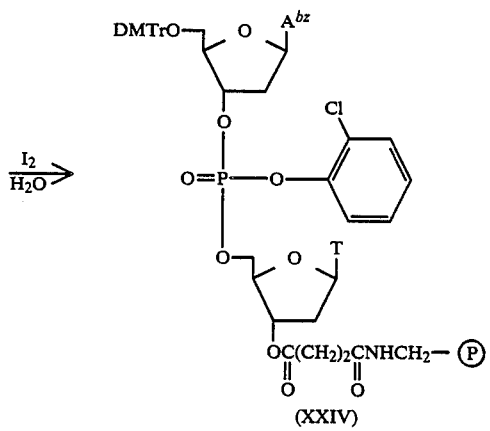

Thymidine bound to polystyrene ⓟ (XXV) (10 mg; 1.2 μmol.), tri-n-butylstannylbenzotriazole (XXVI) (39 mg; 96 μmol.), 1-methylimidazole (XXVII) (9.85 mg; 120 μmol.) and $N^6$-benzoyl-5'-O-dimethoxytrityldeoxyadenosine-3'-O-(2-chlorophenyloxy-2-methylphenylthio)phosphine (I) (23 mg; 24 μmol.) were reacted in the same manner as that described in Example 20. Subsequent oxidation and protective group removal reactions were also carried out as in Example 20. The results of the trityl cation test and HPLC analysis carried out similarly as in Example 19 showed the yield of the above reaction of 99% and the content of dimer of deoxyadenosine and thymidine of 99% in the deprotected product (see FIG. 3).

EXAMPLE 22

Thymidine carried on polystyrene Ⓟ (XXV wherein m=0) (10 mg; 1.2 μmol.), tri-n-propylstannyl-benzotriazole (XXVI) (35 mg. 96 μmol.), 1-methylimidazole (XXVII) (9.85 g; 120 μmol.) and 5'-O-dimethoxytritylthymidine-3'-O-(2-chlorophenyloxy-2-methylphenylthio)phosphine (I) (20 mg; 24 μmol.) were reacted in the same manner as in Example 19. The subsequent oxidation with a mixture of tetrahydrofuran/-pyridine/water (0.45 ml/0.025 ml/0.025 ml) containing iodine (30 mg; 120 μmol.) was also effected as in Example 19. The liqid mixture containing the excess iodine was removed by filtration through a G-4 glass filter and the polystyrene resin left on the filter was washed with pyridine (5 ml×2). Then, a mixture of acetic anhydride (0.18 ml) and pyridine (1.2 ml) containing 4-dimethylaminopyridine (12.2 mg; 100 μmol.) was added to the polystyrene resin and the mixtue was shaken at room temperature for 2 minutes to effect a capping reaction on the 5'—OH group. The excess of said liquid mixture was removed by filtration and the resin left on the filter was washed with 1,2-dichloroethane (5 ml). A 5% trichloroacetic acid (2 ml) in 1,2-dichloroethane was then added to the resin and the mixture was shaken at room temperature for 1 minute to effect the reaction for removing the 5'-dimethoxytrityl group. The excess reagent used was removed by filtration through a G-4 glass filter and the resin left on the filter was washed with pyridine (5 ml) and then with 1,2-dichloroethane (5 ml). To this resin (XXV where m=1) were added compounds (I), (XXVI) and (XXVII) all in the same amounts as those used in the first part of this Example so as to effect the desired coupling reaction similarly. Subsequent oxidation and capping reactions were also carried out in the same manner as above. The resulting resin was washed with 1,2-dichloroethane (5 ml), after which the removal of the protecting dimethoxytrityl group was effected with a 5% trichloroacetic acid in 1,2-dichloroethane to yield thymidine timer carried on polystyrene resin, represented by formula (XXV where m=2). This unit operation was repeated another five times (i.e. until m=7 in (XXV) was attained) to afford thymidine octamer.

The thymidine octamer carried on polystyrene resin Ⓟ was used as starting compound (XXV) for the intended coupling reaction using compounds (I), (XXVI) and (XXVII) above all in the same respective amounts as used in the above and the subsequent oxidation reaction was also effected using iodine in the same amount as above. The resulting resin was washed wit pyridine (5 ml×2) and then with 1,2-dichloroethane (5 ml) and subjected to the trityl cation test as described in Example 19 which showed that the total yield of compound (XXIV) where m=7 was 85%. Subsequently, the removal of protecting groups was carried out in the same manner as in Example 19 using a mixture of p-dioxane (0.9 ml) and water (0.9 ml) containing syn-4-nitrobenzaldoxime (150 mg; 900 μmol.) and 1,1,3,3-tetramethylguanidine (103.5 mg; 900 μmol.) and 80% aqueous acetic acid (2 ml). HPLC analysis of the crude product confirmed the presence of thymidine nonamer (see FIG. 4).

REFERENCE EXAMPLE 1

Preparation of 2-chlorophenyloxy-2-methylphenylthio-1,2,4-triazolylphosphine

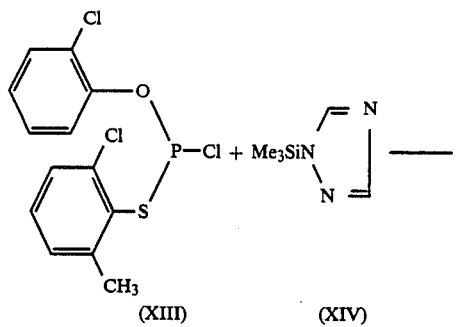

(XIII)    (XIV)

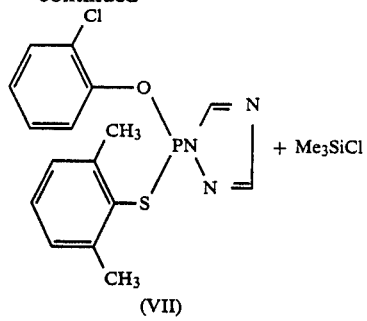

(VII)

A toluene solution (3 ml) containing trimethylsilyl-1,2,4-triazole (XIV) (0.046 g; 0.33 mmol.) was added to a toluene solution (2 ml) containing 2-chlorophenyloxy-2-methylphenylthio-chlorophosphine (XIII) (0.095 g; 0.3 mmol.) at 0° C. and the mixture was stirred at that temperature for 10 minutes. Then, a low-boiling fraction was trapped at −78° C. under a reduced pressure to yield the titled compound (VII) as a residue. The low-boiling fraction so trapped was subjected to fractional distillation to yield trimethylchlorosilane. The result is shown in Table 4.

REFERENCE EXAMPLES 2-3

The procedure of Reference Example 1 was repeated in each of Reference Examples 2-5 except that other chlorophosphine compound (XIII) was used. The nature of starting compounds and the result obtained in each of these Reference Examples are also shown in Table 4.

TABLE 4

| Reference Example No. | Reactants | | Products | | | Me₃SiCl |
| | Chlorophosphine compound (XIII) | Silylazole compound (XIV) | 1,2,4-Triazolylphosphine compound (VII) | | | |
| | | | Yield (%) | Structural formula | ¹HNMR(CDCl₃, TMS): δ(ppm) | Yield (%) |
| 1 | [structure with Cl, O, S, CH₃] | Me₃SiN-triazole | 99 | [structure] | 2.33(s,3H,o-C$\underline{H}$₃C₆H₄S—), 6.75-7.55(m,8H,o-CH₃C₆$\underline{H}$₄S— and o-ClC₆$\underline{H}$₄O—), 8.14(s,1H, 1,2,4-triazolyl, 3-position), 8.44(s,1H,1,2,4-triazolyl, 5-position). | 85 |
| 2 | [structure with CH₃O, P—Cl, S, CH₃] | Me₃SiN-triazole | 99 | [structure with CH₃O, PN-triazole, S, CH₃] | 2.43(s,3H,o-C$\underline{H}$₃C₆H₄S—), 3.72(d,J=10.0Hz,3H,CH₃O—), 6.85-7.55(m,4H, o-CH₂C₆$\underline{H}$₄S—), 8.13(s,1H, 1,2,4-triazolyl, 3-position), 8.43(s,1H,1,2,4-triazolyl, 5-position). | 86 |

TABLE 4-continued

| Reference Example No. | Reactants | | Products | | | $Me_3SiCl$ Yield (%) |
|---|---|---|---|---|---|---|
| | Chlorophosphine compound (XIII) | Silylazole compound (XIV) | 1,2,4-Triazolylphosphine compound (VII) | | | |
| | | | Yield (%) | Structural formula | $^1HNMR(CDCl_3,$ TMS): δ(ppm) | |
| 3 | 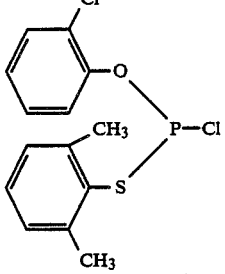 | 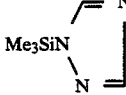 | 99 | 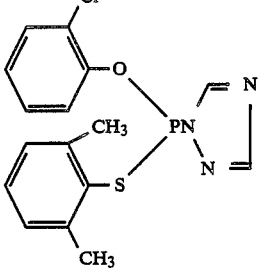 | 2.41(s,6H,2,6-($CH_3$)$_2C_6H_3S$—), 6.75–7.55(m,7H,o-$ClC_6\underline{H}_4O$— and 2,6-$Me_2C_6\underline{H}_3S$—), 8.16(s,1H,1,2,4-triazolyl, 3-position), 8.57(s,1H,1,2,4-triazolyl, 5-position). | 88 |

REFERENCE EXAMPLE 4

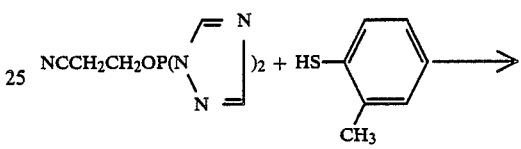

(XV)   (XVI)

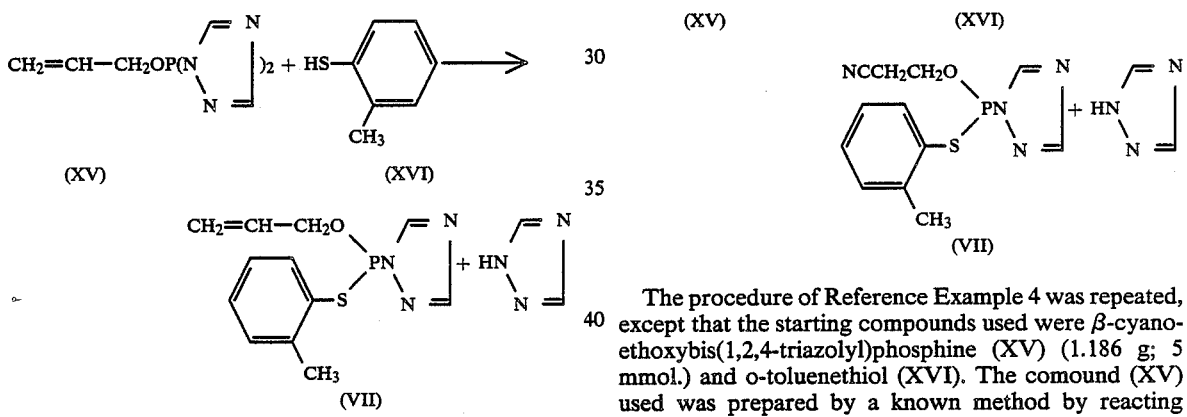

(VII)

o-Toluenethiole (XVI) (0.621 g; 5 mmol.) was added at 0° C. to a solution in chloroform (25 ml) of 2-propenyloxy-bis(1,2,4-triazolyl)phosphine (XV) (1.121 g; 5 mmol.) which was prepared by reacting 2-propenyloxydichlorophosphine with trimethylsilyl-1,2,4-triazole in a known manner. The resulting mixture was stirred at room temperature for 2 hours and then allowed to stand at 0° C. for 30 minutes, during which 1H-1,2,4-triazole formed was desposited as white crystals. The crystals were filtered off and the filtrate was concentrated in vacuo to recover the desired product (VII) as residue. $^1HNMR$ spectrum of the product confirmed the structure of 2-propenyloxy-2-methylphenylthio-1,2,4-triazolylphosphine (VII) above. Yield: 1.33 g; 95%. $^1HNMR$ ($CDCl_3$, TMS) δ: 2.43 (s, 3H, o—$CH_3C_6H_4S$—), 4.30–4.95 (m, 2H, $CH_2$=CH—$CH_2O$—), 5.05–5.45 (m, 2H, $CH_2$=CH—$CH_2O$—), 5.60–6.05 (m, 1H, $CH_2$=CH—$CH_2O$—), 6.95–7.55 (m, 4H, o—$CH_3C_6H_4S$—), 8.18 (s, 1H, 1,2,4-triazolyl, 3-position), 8.46 (s, 1H, 1,2,4-triazolyl, 5-position) ppm.

The 1H-1,2,4-triazole recovered as white crystals as above weighed 0.321 g (yield 95%), m.p. 119°–120° C.

$^1HNMR$ (($CD_3$)$_2SO$, TMS) δ; 8.26 (s, 2H, 3- and 5-positions), 13.5 (s, 1H, 1-position) ppm.

REFERENCE EXAMPLE 5

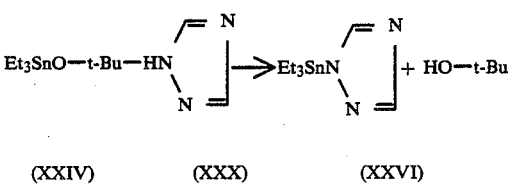

(XV)   (XVI)

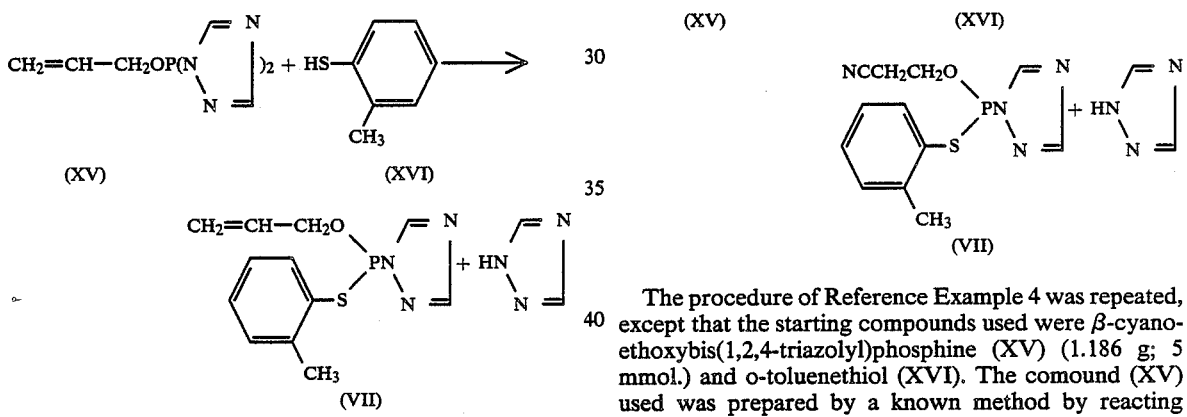

(VII)

The procedure of Reference Example 4 was repeated, except that the starting compounds used were β-cyanoethoxybis(1,2,4-triazolyl)phosphine (XV) (1.186 g; 5 mmol.) and o-toluenethiol (XVI). The comound (XV) used was prepared by a known method by reacting β-cyanoethoxydichlorophosphine with trimethylsilyl-1,2,4-triazole. The desired product, β-cyanoethoxy-2-methylphenylthio-1,2,4-triazolyphosphine (VII) was obtained in an amount of 1.39 g (yield 95%).

$^1HNMR$ ($CDCl_3$, TMS)δ; 2.45 (s, 3H, o—$CH_3C_6H_4S$—), 2.64 (t, J=6.0 Hz, 2H, $NCCH_2CH_2O$—), 3.90–4.75 (m, 2H, $NCCH_2CH_2O$—), 6.90–7.60 (m, 4H, o—$CH_3C_6H_4S$—), 8.18 (s, 1H, 1,2,4-triazolyl, 3-position),8.48 (s, 1H, 1,2,4-triazolyl, 5-postion) ppm.

REFERENCE EXAMPLE 6

$Et_3SnO$—t-Bu—HN⟨triazole⟩ → $Et_3SnN$⟨triazole⟩ + HO—t-Bu (XXIV)   (XXX)   (XXVI)

Triethyl(t-butoxy)stannane (XXIV) (0.098 g; 0.35 mmol.) was added at room temperature to a suspension of 1H-1,2,4-triazole (XXX) (0.024 g; 0.35 mmol.) in deuterochloroform (3.5 ml) and the mixture was stirred at that temperature for 5 minutes. $^1HNMR$ spectrum of the resulting solution showed quantitative formation of triethylstannyl-1,2,4-triazole (XXVI) and t-butanol.

$^1$HNMR (CDCl$_3$, TMS)δ; 0.40–2.10 (m, with a singlet at 1.26 ppm, 24H, (C$_2$H$_5$)$_3$Sn and (CH$_3$)$_3$C), 3.52 (s, 1H, Me$_3$COH), 7.96 (s, 2h, 1,2,4-triazolyl, 3-and 5-positions) ppm.

The addition of acetone (20 ml) to this solution resulted in the deposition of triethylstannyl-1,2,4-triazole (XXVI) in the form of white crystals (0.095 g; yield 99%).

REFERENCE EXAMPLE 7 n-Bu$_3$SnO—t-Bu + HN⟨triazole⟩ (XXIV)  (XXX)  → n-Bu$_3$SnN⟨triazole⟩ + HO—t-Bu (XXVI)

Tri-t-butyl(t-butoxy)stannane (XXIV) (0.127 g; 0.35 mmol.) was added at room temperature to a suspension of 1H-1,2,4-triazole (XXX) (0.034 g; 0.35 mmol.) in deuterochloroform (3.5 ml) and the mixture was stirred at that temperature for 5 minutes. Distillation in vacuo of the reaction mixture to remove the chloroform and t-butanol gave t-n-butylstannyl-1,2,4-triazole (XXVI) as white solid (0.125 g; yield 100%).

$^1$HNMR (CDCl$_3$, TMS) δ; 0.55–2.05 (m, 27H, (C$_4$H$_9$)$_3$Sn), 7.78 (s, 2H, 1,2,4-triazolyl, 3- and 5-postions) ppm.

REFERENCE EXAMPLE 8

Et$_3$SnO—t-Bu + HN⟨imidazole⟩ → Et$_3$SnN⟨imidazole⟩ + HO—t-Bu
(XXIV)   (XXX)   (XXVI)

Triethyl(t-butoxy)stannane (XXIV) (0.098 g; 0.35 mmol.) was added at room temperature to a suspension of imidazole (XXX) (0.024 g; 0.35 mmol.) in chloroform (0.5 ml) and the mixture was stirred at that temperature for 5 minutes. Then, ethyl ether (10 ml) was added to the reaction mixture to result in immediate deposition of white crystals which were confirmed to be triethylstannylimidazole (XXVI) (0.095 g; yield 99%).

$^1$HNMR (CDCl$_3$, TMS)δ; 0.60–2.10 (m, 15H, (C$_2$H$_5$)$_3$Sn), 6.70–7.00 (m, 2H, imidazolyl, 4-and 5-positions), 7.20–7.40 (m, 1H, imidazolyl, 2-position) ppm.

We claim:

1. A phosphorsulfide of a deoxynucleoside or deoxynucleotide of general formula (I):

(I) [structure shown]

wherein $R^1$ is a hydroxy-protecting group; $R^2$ is a phosphate-protecting group; $R^3$ is an aryl group; $B_1$ and $B_2$ may be the same or different and each are a base residue which may have a protecting group; and n is zero or an integer, provided that when n is 2 or larger, the respective $B^2$ may be the same or different.

2. A compound according to claim 1 wherein n is zero.

3. A compound according to claim 1 wherein n is 1.

4. A compound according to claim 1 wherein $R^1$ is a triarylmethyl, pixyl, alkoxycarbonyl, aryloxycarbonyl, arylthioalkyloxycarbonyl or trialkylsilyl group.

5. A compound according to claim 1 wherein $R^2$ is an alkyl, allyl, cyanoalkyl, haloalkyl, arylsulfonylalkyl, aryl or haloaryl group, the alkyl moiety having up to 5 carbon atoms.

6. A compound according to claim 1 wherein $R^3$ is phenyl, 2-methylphenyl, 4-methylphenyl, 2,4-dimethylphenyl, 2,6-dimethylphenyl, 2,4,6-trimethylphenyl, 2-chlorophenyl, 4-chlorophenyl, 3,4-dichlorophenyl or α-naphthyl group.

7. A compound according to claim 1 wherein $B^1$ and $B^2$ each are thymine residue unprotected or protected protected on the 3-position or a, cytosine residue unprotected or protected on the 4-amino group or an, adenine residue unprotected or protected on the 6-amino group or a guanine residue unprotected or protected on the 1-amido, 2-amino and 6-keto groups.

8. A compound according to claim 7 wherein the protecting groups are selected from triarylmethyl, trialkylsilylalkyl, arylthioalkyl, phthaloyl, aryloxycarbonyl, alkoxycarbonyl, dialkylcarbamoyl, diarylcarbamoyl, arylcarbonyl, alkylcarbonyl and 1,2-dialkylcarbonyloxyethylene groups.

9. A compound according to claim 1 selected from:
5'-O-dimethoxytritylthymidine-3'-O-(2-chlorophenyloxy-2-methylphenylthio)phosphine;
5'-O-dimethoxytritylthymidine-3'-O-(methoxy-2-methylphenylthio)phosphine;
5'-O-dimethoxytritylthymidine-3'-O-(2-chlorophenyloxy-2,6-dimethylphenylthio)phosphine;
5'-O-dimethoxytrityl-N$^4$-benzoyl-2'-deoxycytidine-3'-O-(2-chlorophenyloxy-2-methylphenylthio)phosphine;
5'-O-dimethoxytrityl-N$^6$-phthaloyl-2'-deoxyadenosine-3'-O-(2-chlorophenyloxy-2-methylphenylthio)phosphine;

5'-O-methoxytrityl-O⁶-diphenylcarbamoyl-N²-propionyl-2'-deoxyguanosine-3'-O-(2-chlorophenyloxy-2-methylphenylthio)phosphine;

5'-O-dimethoxytritylthymidine-3'-O-(allyloxy-2-methylphenylthio)phosphine; and

5'-O-dimethoxytritylthymidine-3'-O-(2-cyanoethyloxy-2-methylphenylthio)phosphine.

10. A compound according to claim 1 which is selected from:

P-2-chlorophenyl-5'-O-dimethoxytritylthymidyl-3'-O-[(2-chlorophenyloxy-2-methylphenylthio)phosphino]-(3'→5')thymidine;

P-2-chlorophenyl-5'-O-dimethoxytrityl-N⁴-benzoyl-2-deoxycytidyl-3'-O-[(2-chlorophenyloxy-2-methylphenylthio)phosphino]-(3'→5')thymidine;

P-2-chlorophenyl-5'-O-dimethoxytrityl-N⁶-benzoyl-2'-deoxyadenyl-3'-O-[(2-chlorophenyloxy-2-methylphenylthio)phosphino]-(3'→5')thymidine; and P-2-chlorophenyl-5'-O-methoxytrityl-N²-i-butyryl-2'-deoxyguanosinyl-3'-O-[(2-chlorophenyloxy-2-methylphenylthio)phosphino]-(3'→5')thymidine.

11. A process for the preparation of a deoxynucleotide or an oligodeoxynucleotide of general formula (XXIV):

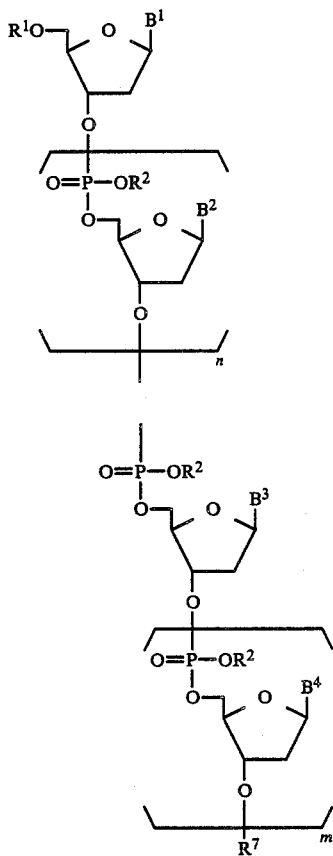

(XXIV)

wherein $R^1$ is a hydroxy-protecting group; $R^2$ is a phoshate-protecting group; $R^7$ is a hydroxy-protecting group which is or is not bonded to a polymer-support; $B^1$, $B^2$, $B^3$ and $B^4$ may be the same or different and each are a base residue which does or does not have a protecting group; n is zero or an integer; and m is zero or an integer, provided that when n or m is 2 or larger, respective $B^2$ or $B^4$ may be the same or different which comprises reacting a phosphorsulfide of a deoxynucleoside or deoxynucleotide of general formula (I):

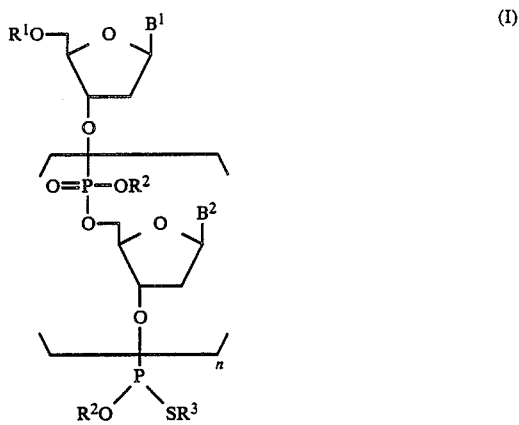

(I)

wherein $R^1$, $R^2$, $B^1$ and $B^2$ and n have the meanings as defined above and $R^3$ is an aryl group with a deoxynucleoside or deoxynucleotide compound of general formula (XXV):

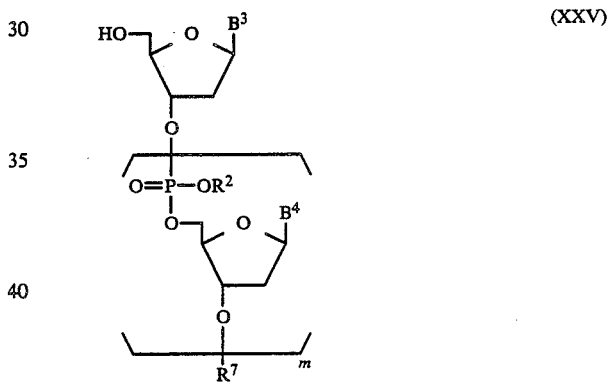

(XXV)

wherein $R^2$, $R^7$, $B^3$, $B^4$ and m have the meanings as defined above in the presence of a trialkylstannyl azole compound of general formula (XXVI) and a base of general formula (XXVII):

$R^8{}_3SnX$            (XXVI)

$R^9NR^{10}{}_2$            (XXVII)

wherein $R^8$ is an alkyl group; $R^9$ is hydrogen atom or an alkyl or aryl group; $R^{10}$ is an alkyl group or $R^{10}$ together with the adjacent nitrogen atom represent a heterocyclic group which may contain one or two additional heteroatoms selected from nitrogen, oxygen and sulfur atoms; and X is an azolyl group, followed by oxidizing the resulting reaction product.

12. A process according to claim 11 wherein said deoxynucleoside phosphorsulfide is of the general formula (IA):

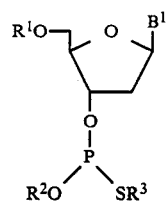 (IA)
13. A process according to claim 11 wherein said dideoxynucleotide phosphorsulfide of general formula (IB):
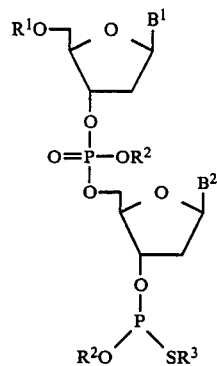 (IB)
* * * * *